(12) United States Patent
Villarete et al.

(10) Patent No.: US 7,695,710 B2
(45) Date of Patent: Apr. 13, 2010

(54) ANTITUMOR AND ANTIVIRAL COMBINATION THERAPIES USING LOW-TOXICITY, LONG-CIRCULATING HUMAN INTERFERON-ALPHA ANALOGS

(75) Inventors: Lorelie H. Villarete, Alameda, CA (US); Chih-Ping Liu, San Francisco, CA (US)

(73) Assignee: Pepgen Corporation, Alameda, CA (US)

( * ) Notice: Subject to any disclaimer, the term of this patent is extended or adjusted under 35 U.S.C. 154(b) by 0 days.

(21) Appl. No.: 11/728,133

(22) Filed: Mar. 23, 2007

(65) Prior Publication Data

US 2007/0237743 A1    Oct. 11, 2007

Related U.S. Application Data

(63) Continuation-in-part of application No. 11/471,788, filed on Jun. 20, 2006.

(60) Provisional application No. 60/692,484, filed on Jun. 20, 2005.

(51) Int. Cl.
*A61K 38/21* (2006.01)
*C07K 14/00* (2006.01)
*C08H 11/02* (2006.01)

(52) U.S. Cl. .................. 424/85.7; 530/351; 530/402
(58) Field of Classification Search .................. None
See application file for complete search history.

(56) References Cited

U.S. PATENT DOCUMENTS

| | | | |
|---|---|---|---|
| 5,281,698 A | 1/1994 | Nitecki | |
| 5,362,852 A | 11/1994 | Geoghegan | |
| 5,382,657 A | 1/1995 | Karasiewicz et al. | |
| 5,711,944 A | 1/1998 | Gilbert et al. | |
| 5,939,286 A | 8/1999 | Johnson et al. | |
| 5,985,265 A | 11/1999 | Kinstler et al. | |
| 6,113,906 A | 9/2000 | Greenwald et al. | |
| 6,174,996 B1 | 1/2001 | Johnson et al. | |
| 6,177,074 B1 | 1/2001 | Glue et al. | |
| 6,204,022 B1 | 3/2001 | Johnson et al. | |
| 6,531,122 B1 | 3/2003 | Pedersen et al. | |
| 6,646,110 B2 | 11/2003 | Nissen et al. | |
| 6,858,409 B1 | 2/2005 | Thompson et al. | |
| 6,872,393 B2 | 3/2005 | Whitlow et al. | |
| 6,982,081 B2 | 1/2006 | Sokawa et al. | |
| 2003/0049277 A1 | 3/2003 | Sokawa et al. | |
| 2003/0130486 A1 | 7/2003 | Villarete et al. | |

FOREIGN PATENT DOCUMENTS

| | | |
|---|---|---|
| EP | 0240224 A2 | 10/1987 |
| WO | WO03/016472 A3 | 2/2003 |
| WO | WO2004/045648 A1 | 6/2004 |
| WO | WO2004/084949 A2 | 10/2004 |

OTHER PUBLICATIONS

Di Marco et al., *Journal of Medical Virology*, 51:17-24 (1997).
Dieterich, Douglas.T., "HCV in HIV: Challenges and Opportunities," http://www.prn.org/prn__nb__cntnt/vo16/num1/dieterich__sum.htm (2001).
Foser et al., *Protein Expression and Purification*, 30:78-87 (2003).
Gomez, M. Romero, *Rev Esp Enferm Dig (Madrid)*, 97(5):299-302 (2005).
Jensen et al., *European Journal of Gastroenterology & Hepatology*, 17(9):899-904 (2005).
Manns et al., *The Lancet*, 358:958-965 (2001).
Motzer et al., *Annals of Oncology*, 13:1799-1805 (2002).
Osborn et al., *The Journal of Pharmacology and Experimental Therapeutics*, 303(2):540-548 (2002).
Reddy et al., *Advanced Drug Delivery Reviews*, 54:571-586 (2002).
Ward et al., *American Family Physician*, 72(4):655-662 (2005).
US 6,884,780, 04/2005, Drummond et al. (withdrawn)

*Primary Examiner*—Prema Mertz
(74) *Attorney, Agent, or Firm*—Judy M. Mohr; Susan L. Harlocker; King & Spalding LLP

(57) ABSTRACT

Interferon-alpha (IFNα) analog proteins modified by chemical attachment of at least one hydrophilic polymer moiety, such as polyethylene glycol chain, are described for use in combination therapies with antiviral and/or antitumor agents. In one embodiment, the IFNα analog protein has an amino acid sequence that differs from a native human IFNα interferon-alpha by one or more amino acid residues in the N-terminal region, comprised of between about residues 1-27, inclusive, by one or more substitutions selected based on the amino acid residue at the corresponding position of a mature interferon-tau (IFNτ) protein. Methods of combination therapy are also described.

6 Claims, 9 Drawing Sheets

|  | 10 | 20 | 27 | | SEQ ID NO: |
|---|---|---|---|---|---|
| CDLPETHSLDNRRTLMLLAQMSRISPS | | | | -- rhIFN-αD | 7 |
| CYLSRKLMLDARENLKLLDRMNRLSPH | | | | -- roIFN-τ | 8 |
| CYLSRKLMLDARENLKLLDRMNRLSPH | | | | -- IFNα-N0 | 11 |
| CYLSRTHSLDNRRTLMLLAQMSRISPS | | | | -- IFNα-N1 | 13 |
| CYLSRKLMLDNRRTLMLLAQMSRISPS | | | | -- IFNα-N2 | 15 |
| CYLSRKLMLDARENLMLLAQMSRISPS | | | | -- IFNα-N3 | 17 |
| CYLSRKLMLDARENLKLLDRMSRISPS | | | | -- IFNα-N4 | 19 |
| CYLSRKLMLDARENLKLLDRMNRLSPH | | | | -- IFNα-N5 | 21 |
| CDLPEKLMLDARENLKLLDRMNRLSPH | | | | -- IFNα-N6 | 23 |
| CDLPETHSLDARENLKLLDRMNRLSPH | | | | -- IFNα-N7 | 25 |
| CDLPETHSLDNRRTLMLLDRMNRLSPH | | | | | |

Fig. 1

SEQUENCE LISTING

<160> NUMBER OF SEQ ID NOS: 49

<210> SEQ ID NO 1
<211> LENGTH: 9
<212> TYPE: PRT
<213> ORGANISM: Homo sapiens

<400> SEQUENCE: 1

Ala Gln Met Ser Arg Ile Ser Pro Ser
1               5

<210> SEQ ID NO 2
<211> LENGTH: 9
<212> TYPE: PRT
<213> ORGANISM: Ovis aries

<400> SEQUENCE: 2

Asp Arg Met Asn Arg Leu Ser Pro His
1               5

```
<210> SEQ ID NO 3
<211> LENGTH: 17
<212> TYPE: PRT
<213> ORGANISM: Homo sapiens

<400> SEQUENCE: 3

Asn Arg Arg Thr Leu Met Leu Leu Ala Gln Met Ser Arg Ile Ser Pro
1               5                   10                  15

Ser

<210> SEQ ID NO 4
<211> LENGTH: 17
<212> TYPE: PRT
<213> ORGANISM: Ovis aries

<400> SEQUENCE: 4

Ala Arg Glu Asn Leu Lys Leu Leu Asp Arg Met Asn Arg Leu Ser Pro
1               5                   10                  15

His

<210> SEQ ID NO 5
<211> LENGTH: 22
<212> TYPE: PRT
<213> ORGANISM: Homo sapiens

<400> SEQUENCE: 5

Thr His Ser Leu Asp Asn Arg Arg Thr Leu Met Leu Leu Ala Gln Met
1               5                   10                  15

Ser Arg Ile Ser Pro Ser
            20

<210> SEQ ID NO 6
<211> LENGTH: 22
<212> TYPE: PRT
<213> ORGANISM: Ovis aries

<400> SEQUENCE: 6

Lys Leu Met Leu Asp Ala Arg Glu Asn Leu Lys Leu Leu Asp Arg Met
1               5                   10                  15

Asn Arg Leu Ser Pro His
            20

<210> SEQ ID NO 7
<211> LENGTH: 27
<212> TYPE: PRT
<213> ORGANISM: Homo sapiens

<400> SEQUENCE: 7

Cys Asp Leu Pro Glu Thr His Ser Leu Asp Asn Arg Arg Thr Leu Met
1               5                   10                  15

Leu Leu Ala Gln Met Ser Arg Ile Ser Pro Ser
            20                  25

<210> SEQ ID NO 8
<211> LENGTH: 27
<212> TYPE: PRT
<213> ORGANISM: Ovis aries
```

```
<400> SEQUENCE: 8

Cys Tyr Leu Ser Arg Lys Leu Met Leu Asp Ala Arg Glu Asn Leu Lys
1               5                   10                  15

Leu Leu Asp Arg Met Asn Arg Leu Ser Pro His
            20                  25

<210> SEQ ID NO 9
<211> LENGTH: 166
<212> TYPE: PRT
<213> ORGANISM: Homo sapiens

<400> SEQUENCE: 9

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 10
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 10

Cys Tyr Leu Ser Arg Lys Leu Met Leu Asp Ala Arg Glu Asn Leu Lys
1               5                   10                  15

Leu Leu Asp Arg Met Asn Arg Leu Ser Pro His Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110
```

```
Asn Ala Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 11
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 11

Cys Tyr Leu Ser Arg Lys Leu Met Leu Asp Ala Arg Glu Asn Leu Lys
1               5                   10                  15

Leu Leu Asp Arg Met Asn Arg Leu Ser Pro His
            20                  25

<210> SEQ ID NO 12
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 12

Cys Tyr Leu Ser Arg Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 13
<211> LENGTH: 27
<212> TYPE: PRT
<213> ORGANISM: Artificial Sequence
<220> FEATURE:
<223> OTHER INFORMATION: Synthetic Polypeptide
```

<400> SEQUENCE: 13

Cys Tyr Leu Ser Arg Thr His Ser Leu Asp Asn Arg Arg Thr Leu Met
1               5                   10                  15

Leu Leu Ala Gln Met Ser Arg Ile Ser Pro Ser
            20                  25

<210> SEQ ID NO 14
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 14

Cys Tyr Leu Ser Arg Lys Leu Met Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 15
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 15

Cys Tyr Leu Ser Arg Lys Leu Met Leu Asp Asn Arg Arg Thr Leu Met
1               5                   10                  15

Leu Leu Ala Gln Met Ser Arg Ile Ser Pro Ser
            20                  25

<210> SEQ ID NO 16
<211> LENGTH: 166
<212> TYPE: PRT
<213> ORGANISM: Artificial Sequence
<220> FEATURE:
<223> OTHER INFORMATION: Synthetic Polypeptide -continued

```
<400> SEQUENCE: 16

Cys Tyr Leu Ser Arg Lys Leu Met Leu Asp Ala Arg Glu Asn Leu Met
1               5                   10                  15

Leu Leu Ala Gln Met Ser Arg Ile Ser Pro Ser Cys Leu Met Asp
            20                  25                  30

Arg His Asp Phe Gly Phe Pro Gln Glu Glu Phe Asp Gly Asn Gln Phe
            35                  40                  45

Gln Lys Ala Pro Ala Ile Ser Val Leu His Glu Leu Ile Gln Gln Ile
        50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 17
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 17

Cys Tyr Leu Ser Arg Lys Leu Met Leu Asp Ala Arg Glu Asn Leu Met
1               5                   10                  15

Leu Leu Ala Gln Met Ser Arg Ile Ser Pro Ser
            20                  25

<210> SEQ ID NO 18
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 18

Cys Tyr Leu Ser Arg Lys Leu Met Leu Asp Ala Arg Glu Asn Leu Lys
1               5                   10                  15

Leu Leu Asp Arg Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
            35                  40                  45

Gln Lys Ala Pro Ala Ile Ser Val Leu His Glu Leu Ile Gln Gln Ile
        50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95
```

-continued

```
Glu Ala Cys Val Met Gln Glu Arg Val Gly Glu Thr Pro Leu Met
                100                 105                 110
Asn Ala Asp Ser Ile Leu Ala Val Lys Lys Tyr Phe Arg Arg Ile Thr
            115                 120                 125
Leu Tyr Leu Thr Glu Lys Lys Tyr Ser Pro Cys Ala Trp Glu Val Val
        130                 135                 140
Arg Ala Glu Ile Met Arg Ser Leu Ser Leu Ser Thr Asn Leu Gln Glu
145                 150                 155                 160
Arg Leu Arg Arg Lys Glu
                165

<210> SEQ ID NO 19
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 19

Cys Tyr Leu Ser Arg Lys Leu Met Leu Asp Ala Arg Glu Asn Leu Lys
1               5                   10                  15
Leu Leu Asp Arg Met Ser Arg Ile Ser Pro Ser
            20                  25

<210> SEQ ID NO 20
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 20

Cys Asp Leu Pro Glu Lys Leu Met Leu Asp Ala Arg Glu Asn Leu Lys
1               5                   10                  15
Leu Leu Asp Arg Met Asn Arg Leu Ser Pro His Ser Cys Leu Met Asp
            20                  25                  30
Arg His Asp Phe Gly Phe Pro Gln Glu Glu Phe Asp Gly Asn Gln Phe
        35                  40                  45
Gln Lys Ala Pro Ala Ile Ser Val Leu His Glu Leu Ile Gln Gln Ile
    50                  55                  60
Phe Asn Leu Phe Thr Thr Lys Asp Ser Ser Ala Ala Trp Asp Glu Asp
65                  70                  75                  80
Leu Leu Asp Lys Phe Cys Thr Glu Leu Tyr Gln Gln Leu Asn Asp Leu
                85                  90                  95
Glu Ala Cys Val Met Gln Glu Arg Val Gly Glu Thr Pro Leu Met
                100                 105                 110
Asn Ala Asp Ser Ile Leu Ala Val Lys Lys Tyr Phe Arg Arg Ile Thr
            115                 120                 125
Leu Tyr Leu Thr Glu Lys Lys Tyr Ser Pro Cys Ala Trp Glu Val Val
        130                 135                 140
Arg Ala Glu Ile Met Arg Ser Leu Ser Leu Ser Thr Asn Leu Gln Glu
145                 150                 155                 160
Arg Leu Arg Arg Lys Glu
                165

<210> SEQ ID NO 21
<211> LENGTH: 27
<212> TYPE: PRT
<213> ORGANISM: Artificial Sequence
```

<220> FEATURE:
<223> OTHER INFORMATION: Synthetic Polypeptide

<400> SEQUENCE: 21

Cys Asp Leu Pro Glu Lys Leu Met Leu Asp Ala Arg Glu Asn Leu Lys
1               5                   10                  15

Leu Leu Asp Arg Met Asn Arg Leu Ser Pro His
            20                  25

<210> SEQ ID NO 22
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 22

Cys Asp Leu Pro Glu Thr His Ser Leu Asp Ala Arg Glu Asn Leu Lys
1               5                   10                  15

Leu Leu Asp Arg Met Asn Arg Leu Ser Pro His Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 23
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 23

Cys Asp Leu Pro Glu Thr His Ser Leu Asp Ala Arg Glu Asn Leu Lys
1               5                   10                  15

Leu Leu Asp Arg Met Asn Arg Leu Ser Pro His
            20                  25

<210> SEQ ID NO 24
<211> LENGTH: 166
<212> TYPE: PRT
<213> ORGANISM: Artificial Sequence
<220> FEATURE:
<223> OTHER INFORMATION: Synthetic Polypeptide

```
<400> SEQUENCE: 24

Cys Asp Leu Pro Glu Thr His Ser Leu Asp Asn Arg Arg Thr Leu Met
1               5                   10                  15

Leu Leu Asp Arg Met Asn Arg Leu Ser Pro His Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Arg Val Gly Glu Thr Pro Leu Met
            100                 105                 110

Asn Ala Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 25
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 25

Cys Asp Leu Pro Glu Thr His Ser Leu Asp Asn Arg Arg Thr Leu Met
1               5                   10                  15

Leu Leu Asp Arg Met Asn Arg Leu Ser Pro His
            20                  25

<210> SEQ ID NO 26
<211> LENGTH: 172
<212> TYPE: PRT
<213> ORGANISM: Ovis aries

<400> SEQUENCE: 26

Cys Tyr Leu Ser Arg Lys Leu Met Leu Asp Ala Arg Glu Asn Leu Lys
1               5                   10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
            100                 105                 110
```

```
Asn Met Asp Pro Ile Val Thr Val Lys Lys Tyr Phe Gln Gly Ile Tyr
            115                 120                 125

Asp Tyr Leu Gln Glu Lys Gly Tyr Ser Asp Cys Ala Trp Glu Ile Val
        130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

<210> SEQ ID NO 27
<211> LENGTH: 527
<212> TYPE: DNA
<213> ORGANISM: Artificial Sequence
<220> FEATURE:
<223> OTHER INFORMATION: Synthetic Gene

<400> SEQUENCE: 27

```
ctaggctcga agagagatgt tacttgtcta gaaagttgat gttggacgcc agagagaact      60
tgaagttgtt ggatagaatg aacagacttt ctcctcactc ttgtcttatg gacagacacg     120
acttcggttt cccacaagaa gaatttgacg gtaaccaatt ccaaaaggct ccagctatct     180
ctgtcttgca cgagttgatc caacaaattt tcaaccttt cactaccaag gactcctccg      240
ctgcttggga cgaagatttg cttgacaagt tctgtactga gctttaccaa caattgaacg     300
acttggaagc ctgtgtcatg caagaagaga gagttggaga ccccctttg atgaacgctg      360
attccatttt ggctgtcaag aagtacttca gaagaattac cttgtacctt actgagaaga     420
agtactctcc atgtgcttgg gaggttgtta agctgaaat tatgagatcc ttgtctttgt      480
ctactaacct tcaagaaaga ttgagaagaa aggagtaagc ggccgcg                   527
```

<210> SEQ ID NO 28
<211> LENGTH: 24
<212> TYPE: DNA
<213> ORGANISM: Artificial Sequence
<220> FEATURE:
<223> OTHER INFORMATION: Synthetic Linker

<400> SEQUENCE: 28

```
ctagaaagtt gatggaattc gacg                                             24
```

<210> SEQ ID NO 29
<211> LENGTH: 25
<212> TYPE: DNA
<213> ORGANISM: Artificial Sequence
<220> FEATURE:
<223> OTHER INFORMATION: Synthetic Linker

<400> SEQUENCE: 29

```
gttaccgtcg aattccatca acttt                                            25
```

<210> SEQ ID NO 30
<211> LENGTH: 135
<212> TYPE: DNA
<213> ORGANISM: Artificial Sequence
<220> FEATURE:
<223> OTHER INFORMATION: Synthetic Nucleic Acid

<400> SEQUENCE: 30

```
tcgagaagag atgttacctt tctagaaccc actccttgga caacagaaga accttgatgt      60
tgctagccca atgtccaga atctcccctt cctcttgtct tatggacaga cacgacttcg      120
gtttcccaca agaag                                                      135
```

<210> SEQ ID NO 31
<211> LENGTH: 135
<212> TYPE: DNA
<213> ORGANISM: Artificial Sequence
<220> FEATURE:
<223> OTHER INFORMATION: Synthetic Nucleic Acid

<400> SEQUENCE: 31
aattcttctt gtgggaaacc gaagtcgtgt ctgtccataa gacaagagga aggggagatt    60
ctggacattt gggctagcaa catcaaggtt cttctgttgt ccaaggagtg ggttctagaa   120
aggtaacatc tcttc                                                   135

<210> SEQ ID NO 32
<211> LENGTH: 100
<212> TYPE: DNA
<213> ORGANISM: Artificial Sequence
<220> FEATURE:
<223> OTHER INFORMATION: Synthetic Nucleic Acid

<400> SEQUENCE: 32
tcgagaagag atgttacttg tctagaaagt tgatgttgga caacagaaga acccttatgc    60
tgctagctca aatgtccaga atctctccat cctcttgtct                        100

<210> SEQ ID NO 33
<211> LENGTH: 116
<212> TYPE: DNA
<213> ORGANISM: Artificial Sequence
<220> FEATURE:
<223> OTHER INFORMATION: Synthetic Nucleic Acid

<400> SEQUENCE: 33
cgaagtcgtg tctgtccata agacaagagg atggagagat tctggacatt tgagctagca    60
gcataagggt tcttctgttg tccaacatca actttctaga caagtaacat ctcttc       116

<210> SEQ ID NO 34
<211> LENGTH: 100
<212> TYPE: DNA
<213> ORGANISM: Artificial Sequence
<220> FEATURE:
<223> OTHER INFORMATION: Synthetic Nucleic Acid

<400> SEQUENCE: 34
tcgagaagag atgttacttg tctagaaagt tgatgttgga cgctagagag aacttgatgc    60
tgctagctca aatgtccaga atttcccctt cttcttgtct                        100

<210> SEQ ID NO 35
<211> LENGTH: 116
<212> TYPE: DNA
<213> ORGANISM: Artificial Sequence
<220> FEATURE:
<223> OTHER INFORMATION: Synthetic Nucleic Acid

<400> SEQUENCE: 35
cgaagtcgtg tctgtccata agacaagaag aaggggaaat tctggacatt tgagctagca    60
gcatcaagtt ctctctagcg tccaacatca actttctaga caagtaacat ctcttc       116

<210> SEQ ID NO 36
<211> LENGTH: 100
<212> TYPE: DNA
<213> ORGANISM: Artificial Sequence
<220> FEATURE:
<223> OTHER INFORMATION: Synthetic Nucleic Acid -continued

<400> SEQUENCE: 36
tcgagaagag atgttacttg tctagaaagt tgatgcttga cgctagagaa aacttgaagc     60
ttttggacag aatgtccaga atttcccat cctcttgtct                          100

<210> SEQ ID NO 37
<211> LENGTH: 116
<212> TYPE: DNA
<213> ORGANISM: Artificial Sequence
<220> FEATURE:
<223> OTHER INFORMATION: Synthetic Nucleic Acid

<400> SEQUENCE: 37
cgaagtcgtg tctgtccata agacaagagg atggggaaat tctggacatt ctgtccaaaa    60
gcttcaagtt ttctctagcg tcaagcatca actttctaga caagtaacat ctcttc       116

<210> SEQ ID NO 38
<211> LENGTH: 135
<212> TYPE: DNA
<213> ORGANISM: Artificial Sequence
<220> FEATURE:
<223> OTHER INFORMATION: Synthetic Nucleic Acid

<400> SEQUENCE: 38
tcgagaagag atgtgacttg ccagaaaagc ttatgttgga cgccagagaa aacttgaaac    60
ttctagacag aatgaacaga ttgtctccac actcttgtct tatggacaga cacgacttcg  120
gtttcccaca agaag                                                   135

<210> SEQ ID NO 39
<211> LENGTH: 135
<212> TYPE: DNA
<213> ORGANISM: Artificial Sequence
<220> FEATURE:
<223> OTHER INFORMATION: Synthetic Nucleic Acid

<400> SEQUENCE: 39
aattcttctt gtgggaaacc gaagtcgtgt ctgtccataa gacaagagtg tggagacaat    60
ctgttcattc tgtctagaag tttcaagttt tctctggcgt ccaacataag cttttctggc  120
aagtcacatc tcttc                                                   135

<210> SEQ ID NO 40
<211> LENGTH: 100
<212> TYPE: DNA
<213> ORGANISM: Artificial Sequence
<220> FEATURE:
<223> OTHER INFORMATION: Synthetic Nucleic Acid

<400> SEQUENCE: 40
tcgagaagag atgtgacttg cctgaaactc acagtctaga cgccagagag aacttgaagc    60
ttttggacag aatgaacaga ttgtctccac actcttgtct                        100

<210> SEQ ID NO 41
<211> LENGTH: 116
<212> TYPE: DNA
<213> ORGANISM: Artificial Sequence
<220> FEATURE:
<223> OTHER INFORMATION: Synthetic Nucleic Acid

<400> SEQUENCE: 41
cgaagtcgtg tctgtccata agacaagagt gtggagacaa tctgttcatt ctgtccaaaa    60
gcttcaagtt ctctctggcg tctagactgt gagtttcagg caagtcacat ctcttc      116

-continued

<210> SEQ ID NO 42
<211> LENGTH: 100
<212> TYPE: DNA
<213> ORGANISM: Artificial Sequence
<220> FEATURE:
<223> OTHER INFORMATION: Synthetic Nucleic Acid

<400> SEQUENCE: 42
tcgagaagag atgtgacttg ccagagaccc actcccttga caacagaaga actttgatgc      60
ttctagacag aatgaacaga ttgtccccac actcttgtct                          100

<210> SEQ ID NO 43
<211> LENGTH: 116
<212> TYPE: DNA
<213> ORGANISM: Artificial Sequence
<220> FEATURE:
<223> OTHER INFORMATION: Synthetic Nucleic Acid

<400> SEQUENCE: 43
cgaagtcgtg tctgtccata agacaagagt gtggggacaa tctgttcatt ctgtctagaa      60
gcatcaaagt tcttctgttg tcaagggagt gggtctctgg caagtcacat ctcttc        116

<210> SEQ ID NO 44
<211> LENGTH: 172
<212> TYPE: PRT
<213> ORGANISM: Artificial Sequence
<220> FEATURE:
<223> OTHER INFORMATION: Synthetic Polypeptide

<400> SEQUENCE: 44

Cys Tyr Leu Ser Glu Arg Leu Met Leu Asp Ala Arg Glu Asn Leu Lys
1               5                   10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170

<210> SEQ ID NO 45
<211> LENGTH: 37
<212> TYPE: PRT
<213> ORGANISM: Ovis aries

```
-continued

<400> SEQUENCE: 45

Cys Tyr Leu Ser Arg Lys Leu Met Leu Asp Ala Arg Glu Asn Leu Lys
1               5                   10                  15

Leu Leu Asp Arg Met Asn Arg Leu Ser Pro His Ser Cys Leu Gln Asp
            20                  25                  30

Arg Lys Asp Phe Gly
        35

<210> SEQ ID NO 46
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 46

Cys Tyr Leu Ser Glu Arg Leu Met Leu Asp Ala Arg Glu Asn Leu Lys
1               5                   10                  15

Leu Leu Asp Arg Met Asn Arg Leu Ser Pro His Ser Cys Leu Gln Asp
            20                  25                  30

Arg Lys Asp Phe Gly
        35

<210> SEQ ID NO 47
<211> LENGTH: 172
<212> TYPE: PRT
<213> ORGANISM: Artificial Sequence
<220> FEATURE:
<223> OTHER INFORMATION: Hybrid Synthetic Protein

<400> SEQUENCE: 47

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Thr Lys Met Gly Gly Asp Leu Asn Ser Pro
                165                 170

<210> SEQ ID NO 48
<211> LENGTH: 165
<212> TYPE: PRT
<213> ORGANISM: Artificial Sequence
```

```
<220> FEATURE:
<223> OTHER INFORMATION: Synthetic Polypeptide

<400> SEQUENCE: 48

Cys Asp Leu Pro Gln Thr His Ser Leu Gly Ser Arg Arg Thr Leu Met
1               5                   10                  15

Leu Leu Asp Arg Met Asn Arg Leu Ser Leu His Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 49
<211> LENGTH: 165
<212> TYPE: PRT
<213> ORGANISM: Homo sapiens

<400> SEQUENCE: 49

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

ANTITUMOR AND ANTIVIRAL COMBINATION THERAPIES USING LOW-TOXICITY, LONG-CIRCULATING HUMAN INTERFERON-ALPHA ANALOGS

CROSS-REFERENCE TO RELATED APPLICATIONS

This application is a continuation-in-part of U.S. patent application Ser. No. 11/471,788, filed Jun. 20, 2006, which claims the benefit of U.S. Provisional Application No. 60/692,484, filed Jun. 20, 2005, which are incorporated herein by reference in their entirety.

TECHNICAL FIELD

The subject matter described herein relates to a polymer-modified interferon-alpha protein analog, to low-toxicity human interferon-alpha analogs having a low rate of clearance from the body, and to methods of treating using these analogs, in combination with anti-tumor or anti-viral agents

BACKGROUND

Interferons (IFNs) are classified into two distinct groups: type I interferons, including IFNα, IFNβ, IFNτ, and IFNω (also known as IFNαII); and type II interferons, represented by IFNγ (reviewed by DeMaeyer, E., et al., INTERFERONS AND OTHER REGULATORY CYTOKINES, John Wiley and Sons, New York (1988)). Human interferon alpha (HuIFNα) is a type I interferon consisting of approximately 25 known distinct subtypes. These HuIFNαs are highly pleiotropic cytokines with broad-spectrum antiviral, antiproliferative, and immunomodulatory properties. Specifically, they inhibit replication of a variety of RNA- and DNA-containing viruses, inhibit the growth of malignant cells, affect the expression of a variety of oncogenes, and activate natural killer cells.

A subtype of HuIFNα, HuIFNα2, has been used in the treatment of various viral diseases and cancers. However, at the doses required for therapeutic effects, patients often suffer from toxic side effects including "flu-like symptoms", malaise, anorexia, neutropenia, and abnormal liver function. Many patients cannot tolerate the side effects and treatment with IFNα is discontinued.

Attempts to provide an IFNα that does not cause intolerable side effects have led to development of, for example, hybrid IFNs, consensus IFNα, and long-acting interferons, such as pegylated IFNα. Examples of IFNαs modified with polyethylene glycol (PEG) include the pegylated interferon alpha-2b (PEG Intron®) and alpha-2a (Pegasys®), where 12 kDa polyethylene glycol or a 40 kDa branched-chain PEG chain, respectively, are attached to the INFα.

However, the safety profiles of these PEG-modified IFNαs were qualitatively similar or worse than those of the corresponding native proteins (Bukowski R. M. et al., Cancer, 95(2):389-96 (2002); Bukowski R. M. et al., Journal of Clinical Oncology; 20(18):3841-3949 (2002); Motzer, R. J. et al., J. Clin. Oncol., 19(5):1312-9 (2001); Tong M. J., Journal of Interferon and Cytokine Research, 18:81-86 (1998); Yao G. B. et al., Journal of Gastroenterology and Hepatolog., 15:1165-1170 (2000); Heathcote E. J. et al, N. Engl. J. Med., 343(23):1673-80 (2000); Tong M. J. et al., Hepatology; 26(3):747-54 (1997)). The most commonly reported adverse effects were nausea, anorexia, fatigue and rigors, the incidence of which were dose-related. In addition, with longer duration of therapy, dose-limiting toxicities including severe fatigue, neurotoxicity, liver function abnormalities, and myelosuppression were observed at doses of 7.5 μg/kg or higher for PEG Intron® (Bukowski R. M. et al., Cancer, 95(2):389-96 (2002)). Even consensus IFNα at a dose of >9 μg was not tolerated by all patients, and a dose reduction was needed for some patients to complete a study (Yao G. B. et al., Journal of Gastroenterology and Hepatolog., 15:1165-1170 (2000)). Thus, the current pegylated forms of IFNαs and consensus IFNα have failed to address the toxicity problems with IFNα therapy.

There remains a need in the art for an improved polymer modified IFNα that can be used alone and/or in combination with known anti-tumor or anti-viral agents.

BRIEF SUMMARY

In one aspect, a composition is provided, the composition comprised of a protein analog of a native human interferon-alpha covalently attached to at least one hydrophilic polymeric chain and an anti-tumor agent or antiviral agent. In some embodiments, the anti-tumor agent or antiviral agent is an anti-tumor agent. In some embodiments, the anti-tumor agent or antiviral agent is an antiviral agent.

In one embodiment, the hydrophilic polymeric chain is polyethylene glycol. The polyethylene glycol can be linear or branched.

In another embodiment, the protein analog is a protein analog of native human interferon-alpha-d. In another embodiment, the protein analog is a protein analog of native human interferon-alpha-2b.

In one embodiment, the sequence of amino acids in the protein analog differs from the sequence of amino acids in native human interferon-alpha 2b at one or more of positions 19, 20, 22, 24, and 27.

In one preferred embodiment, the protein analog has a sequence identified as SEQ ID NO:48.

In another aspect, a method of treating a viral infection is provided. The method comprises administering to a subject suffering from a viral infection, a protein analog of a native human interferon-alpha covalently attached to at least one hydrophilic polymeric chain, said protein analog administered in an amount effective for treatment of the infection, and an antiviral agent.

In one embodiment, the viral infection is a hepatitis viral infection. In specific embodiments, the hepatitis viral infection is a hepatitis C infection.

In the method, the protein analog can be administered parenterally, in one embodiment. The administration can be done at least about weekly, in one embodiment. The dose can vary, but In one embodiment, the protein analog is administered at a weekly dose of at least about 450 μg. In alternative embodiments, the protein analog is administered twice weekly dose of at least about 900 μg.

In yet another aspect, a method for treating a viral infection is provided. The method comprises administering to a subject suffering from a viral infection, a protein analog of a native human interferon-alpha covalently attached to at least one hydrophilic polymeric chain, said protein analog administered at a dose frequency to achieve a substantially steady state plasma concentration of the protein analog, whereby said administering has no cytotoxic effect on hepatocytes.

It is also an embodiment to provide a pharmaceutical composition comprising the chemically modified therapeutic protein, and also kits which comprise the pharmaceutical composition.

It is an additional embodiment to provide a method for treating disease by for example inhibiting tumor growth or viral replication or treating autoimmune disease, using the compositions described herein.

BRIEF DESCRIPTION OF THE DRAWINGS

FIG. 1 shows the alignment of the first 27 N-terminal amino acid residues of mature human IFNαD, mature ovine IFNτ, and eight IFNα analogs designated IFNα-N0 through IFNα-N7.

BRIEF DESCRIPTION OF THE SEQUENCES

Figure 2:
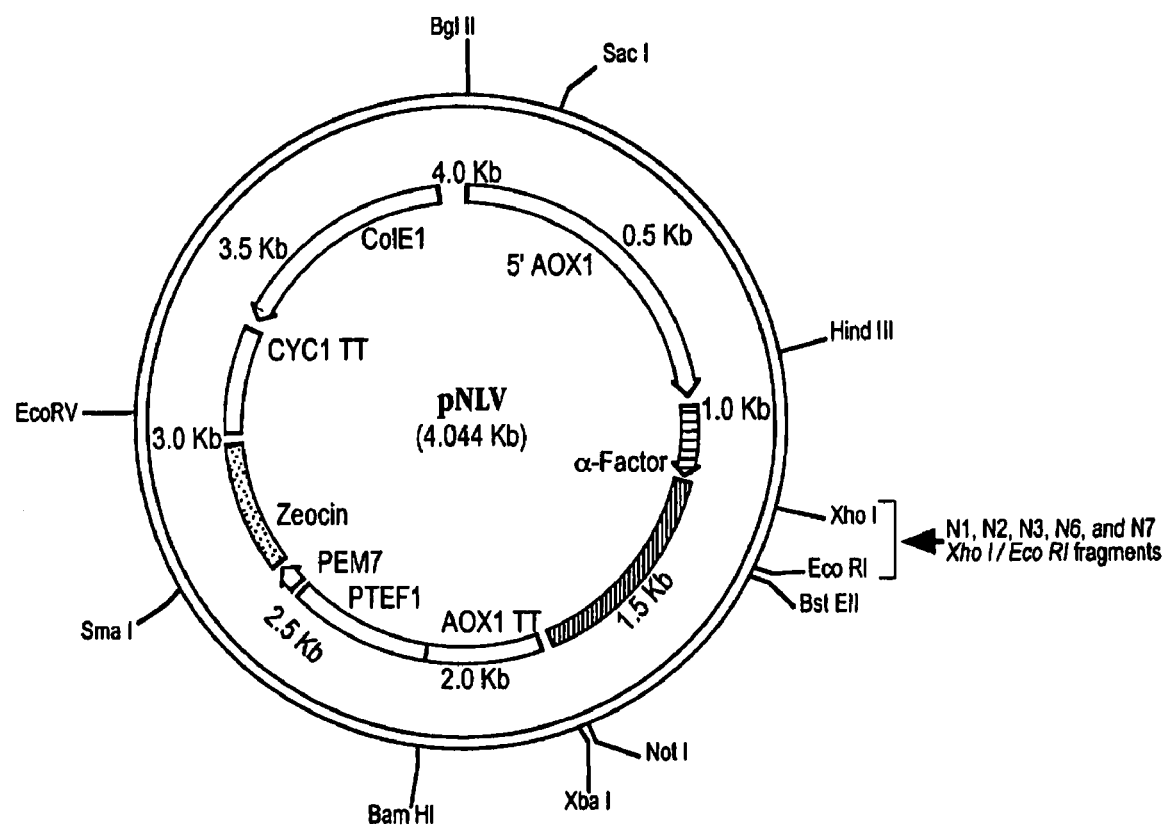
FIG. 2 is a diagram of a vector for preparation of IFNα analogs designated IFNα-N0 through IFNα-N7. A synthetic gene encoding each analog was constructed and inserted into a pPICZα vector to create the expression vector called NLV, and the synthetic genes encoding each analog were constructed by sequential ligation of oligonucleotides creating fragments of about 150 base pairs in length containing the desired nucleotide changes. The nucleotide fragments were then ligated into the XhoI/EcoRI sites of the construct to produce the different analogs in the pPICZα a vector background.

SEQ ID NO:1 is the amino acid sequence of human IFNα (HuIFNα) between residues 19-27.

SEQ ID NO:2 is the amino acid sequence of ovine interferon-tau (OvIFNτ) between residues 19-27.

SEQ ID NO:3 is the amino acid sequence of HuIFNαd between residues 11-27.

SEQ ID NO:4 is the amino acid sequence of OvIFNτ between residues 11-27.

SEQ ID NO:5 is the amino acid sequence of HuIFNαd between residues 6-27.

SEQ ID NO:6 is the amino acid sequence of OvIFNτ between residues 6-27.

SEQ ID NO:7 is the amino acid sequence of HuIFNα between residues 1-27.

SEQ ID NO:8 is the amino acid sequence of OvIFNτ between residues 1-27.

SEQ ID NO:9 is the amino acid sequence of mature HuIFNα (IFNα-d; GenBank Accession No. J00210, PID g386796).

SEQ ID NO:10 is the amino acid sequence of the IFNα analog IFNαd-N0.

SEQ ID NO:11 is the amino acid sequence of the IFNα analog IFNαd-N0 between residues 1-27.

SEQ ID NO:12 is the amino acid sequence of the IFNα analog IFNαd-N1.

SEQ ID NO:13 is the amino acid sequence of the IFNα analog IFNαd-N1 between residues 1-27.

SEQ ID NO:14 is the amino acid sequence of the IFNα analog IFNαd-N2.

SEQ ID NO:15 is the amino acid sequence of the IFNα analog IFNαd-N2 between residues 1-27.

SEQ ID NO:16 is the amino acid sequence of the IFNα analog IFNαd-N3.

SEQ ID NO:17 is the amino acid sequence of the IFNα analog IFNαd-N3 between residues 1-27.

SEQ ID NO:18 is the amino acid sequence of the IFNα analog IFNαd-N4.

SEQ ID NO:19 is the amino acid sequence of the IFNα analog IFNαd-N4 between residues 1-27.

SEQ ID NO:20 is the amino acid sequence of the IFNα analog IFNαd-N5.

SEQ ID NO:21 is the amino acid sequence of the IFNα analog IFNαd-N5 between residues 1-27.

SEQ ID NO:22 is the amino acid sequence of the IFNα analog IFNαd-N6.

SEQ ID NO:23 is the amino acid sequence of the IFNα analog IFNαd-N6 between residues 1-27.

SEQ ID NO:24 is the amino acid sequence of the IFNα analog IFNαd-N7.

SEQ ID NO:25 is the amino acid sequence of the IFNα analog IFNαd-N7 between residues 1-27.

SEQ ID NO:26 is the amino acid sequence of mature OvIFNτ (oTP-1; GenBank Accession No. Y00287; PID g1358).

SEQ ID NO:27 is the nucleotide sequence for the synthetic gene encoding the analog IFNαd-N0.

SEQ ID NO:28 is the nucleotide sequence for Linker1.

SEQ ID NO:29 is the nucleotide sequence for Linker2.

SEQ ID NO:30 is the nucleotide sequence for residues 1-27 of the N1 analog, forward strand.

SEQ ID NO:31 is the nucleotide sequence for Fragment N1, reverse strand.

SEQ ID NO:32 is the nucleotide sequence for Fragment N2, forward strand.

SEQ ID NO:33 is the nucleotide sequence for Fragment N2, reverse strand.

SEQ ID NO:34 is the nucleotide sequence for Fragment N3, forward strand.

SEQ ID NO:35 is the nucleotide sequence for Fragment N3, reverse strand.

SEQ ID NO:36 is the nucleotide sequence for Fragment N4, forward strand.

SEQ ID NO:37 is the nucleotide sequence for Fragment N4, reverse strand.

SEQ ID NO:38 is the nucleotide sequence for Fragment N5, forward strand.

SEQ ID NO:39 is the nucleotide sequence for Fragment N5, reverse strand.

SEQ ID NO:40 is the nucleotide sequence for Fragment N6, forward strand.

SEQ ID NO:41 is the nucleotide sequence for Fragment N6, reverse strand.

SEQ ID NO:42 is the nucleotide sequence for Fragment N7, forward strand.

SEQ ID NO:43 is the nucleotide sequence for Fragment N7, reverse strand.

SEQ ID NO:44 corresponds to an amino acid sequence of mature ovine IFNτ, where the amino acid residues at positions 5 and 6 of the sequence are modified relative to the sequence of SEQ ID NO:26.

SEQ ID NO:45 corresponds to the first 37 amino acid residues of ovine IFNτ, shown in SEQ ID NO:26.

SEQ ID NO:46 corresponds to the first 37 amino acid residues of modified ovine IFNτ, shown in SEQ ID NO:44.

SEQ ID NO:47 is a hybrid interferon protein consisting of a C-terminal region derived from interferon-τ and a region derived from another interferon.

SEQ ID NO:48 corresponds to the amino acid sequence of an IFNα analog referred to herein as IFNα2b-N7 analog, where amino acid residues 19, 20, 22, 24, 27 in the N-terminal region of IFNα2b are substituted with corresponding residues from ovine IFNτ.

SEQ ID NO:49 is the amino acid sequence of human IFNα2b.

DETAILED DESCRIPTION

I. Definitions

Interferon-alpha (IFNα) refers to any one of a family of isolated interferon-alpha proteins, exemplified by INFαD, having an amino acid sequence presented as SEQ ID NO:9, and by IFNα2b sequence, having an amino acid sequence presented as SEQ ID NO:49.

Interferon-tau, abbreviated as IFNτ or interferon-τ, refers to any one of a family of isolated interferon proteins having greater than 70%, or preferably greater than about 80%, or more preferably greater than about 90% amino acid homology to known IFNτ sequences (e.g., Ott, et al., *J. Interferon Res.*, 11:357 (1991); Helmer, et al., *J. Reprod. Fert.*, 79:83 (1987); Imakawa, et al., *Mol. Endocrinol*, 3:127 (1989); Whaley, et al., *J. Biol. Chem.*, 269:10846 (1994); Bazer, et a., WO 94/10313 (1994)). IFNτ sequences have been identified in various ruminant species, including but not limited to, cow (*Bovine* sp., Helmer S. D., *J. Reprod. Fert.*, 79:83 (1987); Imakawa, K., *Mol. Endocrinol.*, 119:532 (1988)), sheep (*Ovine* sp.), musk ox (*Ovibos* sp.), giraffe (*Giraffa* sp., GenBank Accession no. U55050), horse (*Equus caballus*), zebra (*Equus burchelli*, GenBank Accession no. NC005027), hippopotamus (*Hippopotamus* sp.), elephant (*Loxodonta* sp.), llama (*Llama glama*), goat (*Capra* sp., GenBank Accession nos. AY357336, AY357335, AY347334, AY357333, AY357332, AY357331, AY357330, AY357329, AY357328, AY357327), and deer (*Cervidae* sp.). The nucleotide sequences of IFNτ for many of these species are reported in public databases and/or in the literature (see, for example, Roberts, R. M. et al., *J. Interferon and Cytokine Res.*, 18:805 (1998), Leaman D. W. et al., *J. Interferon Res.*, 12:1 (1993), Ryan, A. M. et al., *Anim. Genet.*, 34:9 (1996)).

Ovine IFNτ (OvIFNτ) refers to a protein having the amino acid sequence as identified herein as SEQ ID NO:26, and to proteins having amino acid substitutions and alterations such as neutral amino acid substitutions that do not significantly affect the activity of the protein, such as the IFNτ protein identified herein as SEQ ID NO:44. More generally, an ovine IFN-τ protein is one having about 80%, more preferably 90%, sequence identity to the sequence identified as SEQ ID NO:26. Sequence identity is determined, for example, by a strict amino acid comparison or using one of the many programs commercially available.

"Mature protein" refers to an IFN protein after removal of its leader sequence. For example, the mature IFNτ protein sequence begins with residue Cys 24 of the complete IFNτ amino acid sequence, which corresponds to Cys 1 of the mature protein sequence.

A polynucleotide sequence or fragment is "derived from" another polynucleotide sequence or fragment when it contains the same sequence of nucleotides as are present in the sequence or fragment from which it is derived. For example, a bacterial plasmid contains an insert "derived from" a selected human gene if the sequence of the polynucleotides in the insert is the same as the sequence of the polynucleotides in the selected human gene. Similarly, a polypeptide sequence or fragment is "derived from" another polypeptide sequence or fragment when it contains the same sequence of amino acids as are present in the sequence or fragment from which it is derived.

Percent (%) identity, with respect to two amino acid sequences, refers to the % of residues that are identical in the two sequences when the sequences are optimally aligned and no penalty is assigned to "gaps". In other words, if a gap needs to be inserted into a first sequence to optimally align it with a second sequence, the % identity is calculated using only the residues that are paired with a corresponding amino acid residue (i.e., the calculation does not consider residues in the second sequences that are in the "gap" of the first sequence). Optimal alignment is defined as the alignment giving the highest % identity score. Such alignments can be visually with relatively short polypeptides, or can be preformed using the "GENEWORKS" program. Alternatively, alignments may be performed using the local alignment program LALIGN with a ktup of 1, default parameters and the default PAM.

A "conservative substitution" refers to the substitution of an amino acid in one class by an amino acid in the same class, where a class is defined by common physiochemical amino acid side chain properties and high substitution frequencies in homologous proteins found in nature (as determined by a standard Dayhoff frequency exchange matrix). Six general classes of amino acid sidechains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

A "non-conservative substitution" refers to the substitution of an amino acid in one class with an amino acid from another class; for example, substitution of an Ala, a class II residue, with a class III residue such as Asp, Asn, Glu, or Gln.

"Analog" refers to a polypeptide that is related in sequence to an isolated, native polypeptide by deletion (so-called truncation) or addition of one or more amino acids to the N-terminal and/or C-terminal end of the native protein; deletion or addition of one or more amino acids at one or more sites in the native polypeptide; or substitution of one or more amino acids at one or more sites in the native polypeptide. Such analogs may result from, for example, genetic polymorphism or from human manipulation. Methods for such manipulations are generally known in the art.

"Fusion" protein refers to a protein constructed by appending at least one contiguous portion of a first protein to at least one contiguous portion of a second, different protein. Analogs of fusion proteins, wherein the fusion protein, a chimeric sequence of two different interferons, is assumed to be the native protein. Thus, in an analog of a fusion protein, either or both of the contiguous portions comprising the chimera, one or more amino acid residues may be substituted, deleted or added to the native sequence of such constituent.

The terms "protein" and "polypolypeptide" are used interchangably and refer to a polymer of amino acids and do not refer to a specific length of a polymer of amino acids. This term also includes post-expression modifications of the polypeptide, for example, glycosylations, acetylations, phosphorylations, and the like.

"Conjugate" refers to a compound comprised of a first compound attached or associated with a second compound.

II. Low-toxicity, Long-circulating Human IFNα Analogs

In one aspect, an IFNα analog protein conjugated by covalent attachment to at least one hydrophilic polymer chain is provided. A variety of human IFNα analog proteins are suitable for use, and various examples will be described in this section. In the following section, Section III, methods for conjugating these IFNα analogs to hydrophilic polymers is described.

A. IFNα Analog Proteins

In a first exemplary embodiment, an analog of a native human IFNα protein is provided, wherein the sequence of amino acids in the analog that corresponds to the sequence of residues 1-27 of the native IFNα differs at one or more of positions 19, 20, 22, 24, and 27, provided that the sequence in the analog does not differ from the corresponding native IFN-α by the presence of Ser, Thr, As, Gln, or Gly at the amino acid residue corresponding to position 22. The analog is capable of exhibiting lower toxicity relative to the native IFNα in, for example, an assay involving, for example, human mononuclear cells or hepatocytes in culture.

FIG. 1 shows the first 27 N-terminal amino acid residues of mature HuIFNαD (GenBank Accessn. J00210, PID g386796; SEQ ID NO:9) and mature OvIFNτ (SEQ ID NO:26) where the non-identical residues are shown in bold. HuIFNαD analogs containing certain amino acid substitutions from OvIFNτ were prepared as described in, for example, U.S. Pat. No. 6,204,022, which is incorporated by reference herein in its entirety. FIG. 1 also shows amino acid residues 1-27 of several HuIFNαD analogs, designated IFNα-N0 through IFNα-N7 (SEQ ID NOs:11, 13, 15, 17, 19, 21, 23, 25). IFNα analog proteins having an N-terminal region with amino acid residues 1-27 corresponding to one of analog fragments shown in FIG. 1 and the remainder of the protein (amino acid residues 28-166) corresponding to IFNαD are identified herein by SEQ ID NOs: 10, 12, 14, 16, 18, 20, 22, and 24. These IFNα analogs are all contemplated for use herein, with a protein analog comprising the IFNα-N7 analog fragment (SEQ ID NO:24) being preferred.

Preparation of these analogs is described briefly in Example 1, using the vector shown in FIG. 2. A more detailed description of preparation is provided in U.S. Pat. No. 6,204,022. In vitro cellular toxicity testing of these analogs, also described in U.S. Pat. No. 6,204,022, showed that amino acid residue positions 19, 20, 22, 24, and 27 were involved in reducing the cytotoxicity of mature IFNαD. The amino acid substitutions to one or more of 19, 20, 22, 24, and 27 reduces toxicity, yet the analogs retain the desirable therapeutic properties of the mature native IFNα.

Another IFNα analog protein is described in Example 1B, where human IFNα2b (SEQ ID NO:49, Accession No. AAP20099) was modified at amino acid residue positions 19, 20, 22, 24, and 27 to contain the corresponding ovine IFNτ residues at these positions. This IFNα2b analog protein is identified herein as SEQ ID NO:48. Specifically, the following amino acid residues in IFNα2b were modified as follows: $A^{19} \rightarrow D$; $Q^{20} \rightarrow R$; $R^{22} \rightarrow N$; $I^{24} \rightarrow L$; and $F^{27} \rightarrow H$.

More generally, IFNα analogs based on any IFNα subtype are contemplated. The native IFNα protein can be modified to include one or more of the following substitutions, to arrive at an IFNα analog: amino acid 19 of a mature HuIFNα may be substituted with Asp as position 19 of mature OvIFNτ, or with a same-class residue Asn, Gln, or Glu; amino acid 20 of a mature HuIFNα may be substituted with Arg at position 20 of a mature OvIFNτ or with a same-class residue His or Lys; amino acid 22 of a mature HuIFNα may be substituted with Asn at position 22 of a mature OvIFNτ or with a same-class residue Asp, Gln, or Glu; amino acid 24 of a mature HuIFNα may be substituted with Leu at position 24 of a mature OvIFNτ or with a same-class residue Val or Met; and amino acid 27 of a mature HuIFNα may be substituted with His at position 27 of a mature IFNτ or with a same-class residue Arg or Lys. Such substitutions are effective to reduce the toxicity of the HuIFNα protein but do not significantly alter desirable therapeutic properties.

Other exemplary sequences which encompass the altered positions of some additional exemplary HuIFNα analog proteins include the sequences presented herein as SEQ ID NO:2, SEQ ID NO:4, and SEQ ID NO:6. Most preferred embodiments are HuIFNα analogs having one or more amino acids residues selected from residues 19-27, inclusive, substituted. In another embodiment, an IFNα analog is provided where one or more amino acid residues (i) in the region identified in FIG. 1 by residues 19-27, (ii) wherein the residue is non-identical to a mature IFNτ (preferably mature ovine IFNτ), being substituted with a residue in a mature IFNτ protein. For example, analog proteins where amino acids 19-27 of a mature human IFNα (SEQ ID NO:1, SEQ ID NO:49) are substituted for amino acids 19-27 of mature OvIFNτ (SEQ ID NO:2), result in the alteration of positions 19, 20, 22, 24, and 27 in the mature human IFNα, while the remaining mature human IFNα sequence remains unchanged. Examples correspond to the analogs referred to herein as IFNαd-N7 (SEQ ID NO:24) and IFNα2b-N7 (SEQ ID NO:48).

In another embodiment, the IFNα analog protein is comprised of nonconserved amino acids residues substituted for one or more of the amino acids at positions 19, 20, 22, and 27 of human IFNα. The substituting may include, but is not limited to, substituting a class III amino acid, in particular Asp, for the amino acid at position 19; substituting a class IV amino acid, in particular Arg, for the amino acid at position 20; substituting a class III amino acid, in particular Asn, for the amino acid at position 22; and substituting a class IV amino acid, in particular His, for the amino acid at position 27. In another embodiment, the substituting may include substituting a class V amino acid, in particular Leu, for the amino acid at position 24.

An exemplary analog involves substituting the sequence of mature HuIFNα between residues 19-27, with a 9-mer defined by SEQ ID NO:2. In particular, the sequence of mature HuIFNα between residues 19-27 is SEQ ID NO:1. The 9-mer SEQ ID NO:2 corresponds to residues 19-27 of mature ovine interferon-tau (OvIFNτ) and contains residues non-identical to mature HuIFNα at positions 19, 20, 22, 24, and 27. In another embodiment, the analog involves substituting the sequence of HuIFNα between residues 11-27 with a 17-mer defined by SEQ ID NO:4. In particular, the sequence of mature HuIFNα between residues 11-27 is SEQ ID NO:3. The 17-mer SEQ ID NO:4 corresponds to residues 11-27 of mature OvIFNτ, and contains residues non-identical to HuIFNα at positions 11, 13, 14, 16, 19, 20, 22, 24, and 27. In another embodiment, the analog involves substituting the sequence of HuIFNα between residues 6-27 with a 22-mer defined by SEQ ID NO:6. In particular, the sequence of mature HuIFNα between residues 6-27 is SEQ ID NO:5. The 22-mer SEQ ID NO:6 corresponds to residues 6-27 of mature OvIFNτ, and contains residues non-identical to HuIFNα at positions 6, 7, 8, 11, 13, 14, 16, 19, 20, 22, 24, and 27.

It will be appreciated that although the low-toxicity human IFNα analogs described are "mature" proteins, that is, they begin with residue Cys 24 of the complete interferon sequence (which corresponds to Cys 1 of the mature protein), IFNα analogs which contain the leader sequence, i.e., that begin with the initiation methionine, are also suitable. The leader sequence in such human IFNα analogs may be derived from human IFNα, ovine IFNτ, or another type I interferon.

As noted above, these HuIFNα analogs have a reduced toxicity relative to native human IFNα, and in most cases, may have the same biological activity as the native human IFNα.

B. IFN-α Analog Proteins: Fusion or Hybrid Proteins

In another embodiment, the IFNα protein that is chemically modified with a hydrophilic polymer is a fusion protein comprised of an IFNα protein and an IFNτ protein. As will now be described, an IFNα, such as IFNαD or IFNα2b, can be modified at either the N-terminus or the C-terminus with a contiguous segment of amino acid residues, having any length, from an IFNτ. Several exemplary embodiments will be described, however it will be understood that these are merely exemplary and other fusion or hybrid proteins will be apparent to one of skill in the art. The terms fusion and hybrid are used herein to intend the concept of joining a segment of a first protein to a segment of a second protein. These hybrid or fusion proteins fall within the more general term of an IFN-α analog protein.

A fusion protein comprised of a first segment that contains the N-terminal amino acid sequence of an interferon-tau protein and a second segment that contains the C-terminal amino acid sequence of a non-tau interferon type I polypeptide is contemplated. The two segments are joined in the region of a mature interferon polypeptide between about residues 8 and 37. In another general embodiment, the two segments are spliced in a region corresponding to the portion of a mature interferon polypeptide between about residues 8 and 28. In yet another general embodiment, the two segments are spliced in a region corresponding to the portion of a mature interferon polypeptide between about residues 8 and 22. In still another general embodiment, the two segments are spliced in a region corresponding to the portion of a mature interferon polypeptide between about residues 8 and 16.

Figure 3:
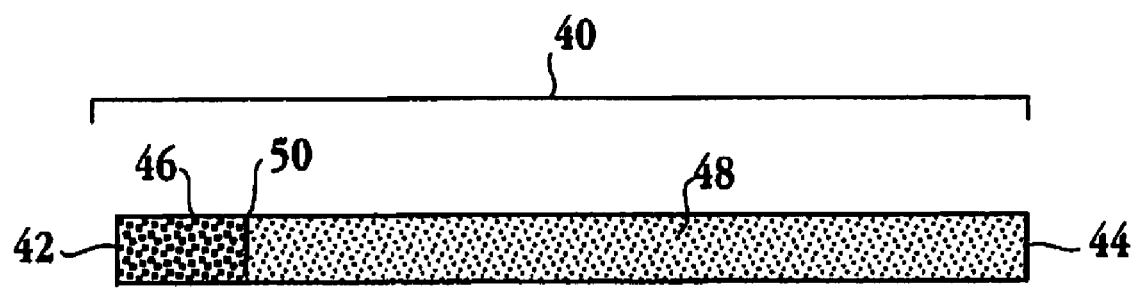
FIG. 3 is a schematic illustration of an exemplary hybrid interferon fusion protein.

As described in U.S. Pat. No. 5,939,286, incorporated by reference herein, the N-terminal region of IFNτ confers decreased toxicity to IFNτ, therefore the N-terminal region of IFNτ is particularly attractive to use in a fusion or hybrid protein. With reference to FIG. 3, such a hybrid interferon fusion protein or polypeptide 40, encoded by a chimeric nucleic acid molecule, has an N-terminus 42 and a C-terminus 44. The fusion protein is made up of a first (N-terminal) segment 46 and a second (C-terminal) segment 48. The N-terminal segment contains the N-terminal amino acid sequence of an interferon-tau polypeptide encoded by a 5' end segment of a chimeric nucleic acid molecule. The C-terminal segment contains the C-terminal amino acid sequence of a non-tau interferon type I polypeptide and amino acid sequence of an interferon-tau polypeptide encoded by a 3' end segment of the chimeric nucleic acid molecule. The two segments are joined or spliced at a junction point 50 which is in a region (unction region) corresponding to the portion of a mature interferon polypeptide between about amino acid residues 8 and 37. Note that the mature IFNτ polypeptide typically begins with a cysteine at amino acid 24 of the complete sequence (which includes the leader sequence and begins with a methionine).

The junction region is typically contained in the 37 amino acid N-terminal peptide of IFN-τ (SEQ ID NO:45 and SEQ ID NO:46). An alignment of the mature amino acid sequences of several IFNτ, IFNα, and IFNβ clones between amino acids 1 and 37 revealed that the greatest degree of divergence among the sequences occurs close to the N-terminus. In particular, the highest degree of divergence between sequences occurs between amino acids 1 and 16, with an intermediate degree of divergence between amino acids 17 and 28. The region between amino acids 29 and 37 is relatively well-conserved among the different type-I interferons. The optimal junction, i.e., the amino acid residue position upstream of which (towards the N-terminal or 5' end) the sequence corresponds to IFNτ, and downstream of which (towards the C-terminal or 3' end) it corresponds to another interferon, e.g., IFNα or IFNβ can be identified, e.g., using peptides or DNA sequences encoding peptides corresponding to longer and shorter regions within IFNτ (1-37), in combination with the functional assays known in the art (such as, antiviral, antiproliferative and cytotoxicity assays). It is contemplated that, for example, that a hybrid or chimeric interferon containing amino acids 1-28 of IFNτ and the remaining amino acids from a non-tau type I interferon possesses the low toxicity associated with interferon tau along with the biological activity associated normally ascribed to such a type I interferon. For example, an IFNτ/IFNα fusion hybrid may, for example, reduce the toxicity of IFNα but not interfere with IFNα antiviral properties.

Exemplary sequences from which the first 8-37 amino acids of the interferon fusion protein may be selected include the sequences corresponding to the following contiguous segments from IFNτ: 1-8, 1-9, 1-10, 1-11, 1-12, 1-13, 1-14, 1-15, 1-16, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, and 1-36, as well as 1-37. It will be appreciated these contiguous segments can be modified, for example, with conservative amino acid substations, and still fall within the fusion proteins contemplated herein.

The remaining sequence (i.e., the amino acid sequence of the "second", C-terminal segment, which is encoded by 3' end segment of the chimeric nucleic acid molecule) may be selected from any suitable non-tau interferon type I polypeptide, such as interferon alpha (e.g., alpha-1 or alpha-2), interferon beta, interferon omega, a hybrid interferon or a consensus interferon. Sequences for non-tau type I interferons are known in the art. Exemplary sequences of consensus interferons are also known (U.S. Pat. No. 4,897,471). Exemplary IFNα sequences are presented in E.P. Patent No. 88622; U.S. Pat. No. 4,820,638; U.S. Pat. No. 4,780,530; and U.S. Pat. No. 4,748,233. Additional interferon alpha and beta sequences are provided in Fish, E. N., *J. Interferon Res.*

12:257-266 (1992). Suitable sequences may also be obtained from GenBank or other public sequence depository.

Determination of the non-tau type I interferon amino acid residue position with which the 3'-end or C-terminal segment begins is accomplished by optimally-aligning the parent sequences and engineering a junction such that the sequence of the resulting chimeric interferon molecule is aligned perfectly with (i) the interferon tau parent sequence in the 5' end or N-terminal segment, and (ii) the non-tau type I interferon parent sequence in the 3' end or C-terminal segment. The parent sequences, of course, are the interferon sequences from which the 5' end or N-terminal segment and the 3' end or C-terminal segment are derived.

The residue position in the non-tau type I interferon with which the 3'-end or C-terminal segment begins is typically the number following the last amino acid residue of the 5'-end or N-terminal IFN-tau segment. For example, in a hybrid interferon fusion protein where the first ten amino acids have the sequence of the first ten amino acids of SEQ ID NO:26, the remaining amino acids may have the sequence of mature interferon alpha (e.g., IFN-αCon$_1$ as described in Fish, Id.) minus the first ten amino acids of the interferon alpha. Another example is where the first 28 amino acids have the sequence of the first 28 amino acids of the IFNτ identified as SEQ ID NO:44, and the remaining amino acids have the sequence of a native, mature interferon, such as IFNαD (SEQ ID NO:9).

It will be appreciated that although the interferon fusion proteins described are "mature" proteins, that is, they begin with residue 24 of the complete interferon sequence, the invention also includes fusion proteins and chimeric nucleic acid molecules encoding fusion proteins that contain the leader sequence, i.e., that begin with the initiation methionine. The leader sequence in such interferon fusion proteins may be derived from either a tau or non-tau type I interferon.

Further, it will be understood that the sequences of both the first and second fragments may be "consensus" sequences. In other words, the sequence of the 5' segment, might not correspond to a "natural" IFNτ, but to a consensus sequence obtained by comparing aligned sequences from several different IFNτs. Similarly, the sequence of the 3' segment, might not correspond to a "natural" non-tau type I IFN, but to a consensus sequence obtained by comparing aligned sequences from several different non-tau type I IFNs.

Alternatively, the sequence of either fragment may correspond to an "internally-consistent" sequence, i.e., to a sequence where each position in the sequence contains a residue that is found in at least one naturally-occurring isoform of either an IFNτ (for the N-terminal segment) or a non-tau type I IFN (for the C-terminal segment) at that position, but where the final sequence corresponds to neither any naturally-occurring isoform nor to any consensus sequence. For example, if two isoforms, each 3 amino acids in length, have the sequences "C R S" and "C K G", an internally-consistent sequence is "C R G".

Furthermore, it will be appreciated that complex chimeras, e.g., chimeras containing more than one discrete region derived from IFNτ and/or more than one region from another suitable interferon, are contemplated. Such chimeras may arise, for example, in cases where the non-tau type I interferon comprising the second (C-terminal) segment is itself a hybrid interferon formed of, e.g., an alpha interferon and a beta interferon (U.S. Pat. No. 4,758,428), an alpha-1 and an alpha-2 interferon (U.S. Pat. No. 4,892,743) or an alpha interferon and an omega interferon (U.S. Pat. No. 4,917,887).

Chimeric nucleic acid molecules may be produced synthetically or with standard molecular protocols and manipulations. DNA sequences encoding the parent polypeptides (the two polypeptides from whose sequences the two segments forming the hybrid protein are derived) are cloned adjacent one another in an expression vector using standard recombinant methods (e.g., by engineering restriction sites which do not alter the translated amino acid sequence into the DNA sequences, digesting the plasmids, and cloning the appropriate fragments into the selected expression vector).

In another embodiment, hybrid interferon proteins consisting of a C-terminal region derived from interferon-τ and a region derived from another interferon are contemplated for use as a protein for chemical modification with a hydrophilic polymer. As described in U.S. Publication No. 2003/0130486, incorporated by reference herein, such hybrid proteins have a C-terminal region of IFNτ and an N-terminal portion derived from a non-tau interferon type I polypeptide, such as IFN-β and the various isoforms of IFN-α. An exemplary protein is identified herein as SEQ ID NO:47. Such a protein may be encoded by a chimeric nucleic acid molecule or produced via native chemical ligation, has an N-terminus comprising from amino acid position 1 to amino acid position 163 of IFN-αD, and a C-terminus comprising from amino acid position 163 to amino acid position 172 of IFN-τ. The N-terminal segment contains the N-terminal amino acid sequence of a non-τ interferon polypeptide which may be encoded by a 5' end segment of the chimeric nucleic acid molecule. The C-terminal segment contains the C-terminal amino acid sequence of an IFN-τ polypeptide which may be encoded by a 3' end segment of the chimeric nucleic acid molecule.

The optimal junction or amino acid residue position upstream of which the sequence corresponds to non-τ interferon, and downstream of which corresponds to IFN-τ can be identified by the known methods, using peptides or DNA sequences encoding peptides corresponding to longer and shorter regions within or extending beyond the IFN-τ (163-172), in combination with a functional assays, such as an antiviral assay or a toxicity assay. A hybrid or chimeric interferon containing amino acids 1-166 of human IFN-αD and the 10 final C-terminal amino acids of IFN-τ possesses the low toxicity associated with interferon tau along with the biological activity associated or normally ascribed to IFN-α. For example, an IFN-α/IFN-τ hybrid may, for example, reduce the toxicity of IFN-α but not interfere with, or even increase, IFN-α antiviral properties. One preferred fusion protein is where the sequence of the N-terminal segment is derived from human IFN-αD, and the C-terminal segment is derived from ovine IFN-τ.

III. Methods for Modifying with a Hydrophilic Polymer

This section describes various synthetic reaction schemes for modifying the above-described proteins with hydrophilic polymer compounds. For simplicity, the term "IFNα analog protein" or "analog protein" in this section intends any of the IFN-α analog proteins described in Section II above, such as the IFNα analogs having certain specific residue substitutions and the exemplary fusion or hybrid proteins having contiguous segments or cassettes of one protein replacing certain residues of or combined with another protein.

The analog proteins described herein may be modified by associating with that analog protein either synthetic or naturally-occurring polymers, oligomers, small molecules or functional groups, thereby producing a combination that is not naturally-occurring. The association of components may be by non-covalent means, such as electrostatic binding or Van der Waals forces, but is advantageously done by covalent bonding between or among the components. Covalent bonding provides the benefit of having a complex that is more readily manipulated and used in various chemical milieu without dissociating because of the strength of the covalent bond, as is readily understand by those skilled in the art. Covalent modification of proteins with one or more other molecules is generally referred to as "conjugation", and the combination product as a "modified protein".

Modifications to the analog protein can be made at any one or more of functional groups present in the analog protein. Numerous functional groups are exposed on the IFNα analog protein exterior, and these groups can be readily functionalized, or converted to groups that can be functionalized, by methods known in the art. The number and nature of the modifications will depend upon the particular properties and structure of the analog protein, and the type of effect desired in the conjugate product. Also, where a substantially homogeneous product is desired, site-selective modification is advantageous, and will in great part determine the type of reaction chemistry used as well as the choice of functional group of the analog protein that will be the site of conjugation. Two particularly convenient sites for selective conjugation are the N-terminus and the C-terminus of the analog protein. Of these two, the N-terminus is generally more readily site-selectively modified because whereas amino acid side chains bearing a carboxylic acid possess roughly the same chemical reactivity as the C-terminus carboxylic group, under readily controlled reaction conditions, the amino group of a lysine residue will not react under conditions in which the N-terminal amino group is active. Other functional groups present, such as the sulfhydryl group of cysteine, or the hydroxyl group of threonine, also provide sites for conjugation reactions.

Knowledge of the amino acid sequence of a protein, aided by a crystal structure showing the three dimensional structure of the protein determines which sites are available for conjugation on the surface of the protein. With respect to the IFNα analog proteins described herein, the crystal structure of IFNτ was published and compared with the structure of IFNα, by Radhakrishnan et al. (*J. Mol. Biol.*, 286:151-162 (1999)). The crystal structure of the native proteins can be used to guide site specific modification of an IFNα analog protein.

Hydrophilic polymers are particularly advantageous for use in preparing the modified IFNα analog protein. Hydrophilic polymers maintain the solubility of the conjugate in aqueous systems such as blood and serum and are suitable for use in therapeutic applications. Suitable polymeric molecules to conjugate to the analog protein include polyethylene glycol (PEG) and common derivatives such as monomethoxy polyethylene glycol (mPEG), polyethylene oxide (PEO), polyvinyl alcohol, polypropylene glycol, polyamine acids, polyvinylpyrrolidone, dextran, polysaccharides, cellulose and cellulose derivatives such carboxymethyl or carboxyethyl cellulose, and starch and starch dervitives. One preferred molecule is PEG due to its ready availability in chemically activated and protected forms, as well as its availability in a range of molecular weights.

PEG has been used numerous times in the conjugation of proteins, including interferon proteins. Disclosures include U.S. Pat. No. 5,711,944 and U.S. Pat. No. 5,281,698, which are incorporated by reference herein. Interferon-beta conjugates are disclosed in U.S. Pat. No. 6,800,735 and U.S. Pat. No. 6,531,122, which are incorporated by reference herein.

The molecular weight of the polymer is contemplated to be in the range of 100 to 500,000 Daltons. More preferably the polymer molecular is between about 10,000 and 50,000 Daltons. The molecular weight used is a function of the number of the polymers per conjugate, the desired hydrodynamic radius of the conjugate, as well as the sensitivity of the protein active site to steric interference by the conjugated polymer.

The polydispersity is also a factor in the choice of the polymer for the conjugate. A narrow polydispersity indicates the polymers are relatively close in size and molecular weight. Use of a narrow distribution leads to a conjugate product that is more uniform and homogeneous.

Linear or branched polymers are contemplated for use. Branched polymers offer the benefit of providing greater steric bulk and size of the conjugate while requiring fewer sites of conjugation on the protein.

Site selective conjugation reactions are also contemplated. One exemplary site is N-terminal modification of the protein. A conjugation reaction using PEG under reduction alkylation conditions in provided in U.S. Pat. No. 5,985,265, incorporated by reference herein. Under this methodology, one polymer will be attached to each protein. Here also, the use of a branched PEG compound or other hydrophilic polymer is contemplated.

Various conjugation chemistries have been used to couple PEG and PEG-like derivatives to proteins. The following methods are exemplary and not limiting in any manner. Other methods may find use, such as those that are taught by Zalipsky, S., et al. (*Biotechnology and Applied Biochemistry*, 15:100-114 (1992)) and in U.S. Pat. No. 5,985,265 that discloses reductive alkylation of a PEG molecule to the N-terminus of a protein. A thiol-selective reaction produced conjugates with polymers appended to the cysteine moieties of a protein using orthopyridyl disulfide as the activating agent in U.S. Pat. No. 6,638,500. In another instance, a functional group was created in situ in the protein by oxidation of a 2-hydroxyethylamine moiety to create an aldehyde group which was then reacted with hydrazine to produce the conjugate, in U.S. Pat. No. 5,362,852.

Other methods for preparing activated PEG and PEG-like derivatives, and proteins having functional groups available for reaction with such derivatives are well-known in the art and are contemplated for in modification of the IFNα analog proteins described herein. Such other methods include those set forth in U.S. Patent Application Nos. 2005/0014240 and 2004/0062746; PCT Application Nos. WO 2004/060300 and WO 2004/060299; and U.S. Pat. No. 6,783,965, all of which are incorporated by reference herein.

In studies conducted the IFNα analog protein referred to herein as the IFNα2b analog (SEQ ID NO:48) was modified with a branched poly(ethylene glycol), as an exemplary hydrophilic polymer according to the procedure described in Example 1C. The exemplary PEG-IFNα2b-N7 analog protein was characterized in vitro and in vivo, as described in Examples 2-7.

IV. Methods of Use

A. Treatment with IFN Analogs

The modified IFN-α protein analogs described herein find use in treating any condition response to treatment with IFNα or IFNτ. This includes, but is not limited to, conditions selected from viral infections, disorders characterized by cellular proliferation, inflammatory conditions, and autoimmune disorders.

In a preferred embodiment, the modified IFNα analog protein is used for treating a viral infection, such as a hepatitis infection, including hepatitis A, hepatitis B, or hepatitis C. Examples 8 and 9 described studies where the PEG-modified INFα analog protein, PEG(40 kDa)-IFNα2b-N7, is used to treat subjects suffering from a viral infection.

In a preferred embodiment, the polymer-modified IFNα analog protein is used for treating a hepatitis C virus (HCV)

infection in a human subject. Cirrhosis leading to liver failure and increased risk for hepatocellular carcinoma are significant morbidities associated with HCV infection. Factors predictive of progression from chronic hepatitis-C to cirrhosis include high levels of viremia, male gender, age more than 40 years at the time of infection, co-infection with HIV1 or HBV, high alcohol consumption, and, the genotype of the virus implicated.

A person suffering from chronic hepatitis C infection may exhibit one or more of the following signs or symptoms: (a) elevated serum alanine aminotransferase (ALT) levels, (b) a positive test for anti-HCV antibodies, (c) the presence of HCV-RNA in the serum, (d) clinical stigmata of chronic liver disease, and/or (e) hepatocelluar damage.

HCV is divided among six genotypes with numerous subtypes, and in one embodiment, the polymer-modified IFNα analog protein is intended for treating an infection due to genotype 2 or genotype 3. Accordingly, a treatment method is contemplated wherein a polymer-modified IFNα analog is administered to an HCV patient, for treatment of the viral infection or to reduce the progression of liver failure.

In another embodiment, the polymer-modified IFNα analog protein is administered to achieve a continuous exposure to the analog protein, for a sustained viral response and for eradication of HCV. Early viral response, defined as minimum 2-log decrease in viral load during first 12 to 24 weeks of treatment, has been identified as good predictor of response. Persons suffering from an HCV infection that are responsive to treatment with the polymer-modified IFNα analog protein can be identified as those who respond to treatment during the first 12-weeks of dosing, by showing a reduction in liver enzymes or at least a 2-log drop in HCV viral load. For example, HCV subjects that demonstrate a viremic response of >1.39 log10 reduction within about 2 weeks after treatment initiation are responsive to the therapy.

The polymer-modified IFNα analog protein is also contemplated for use in treating disorders associate with cellular proliferation, such as solid tumors. In another embodiment, the polymer-modified IFNα analog protein is used for treating an autoimmune condition, such as multiple sclerosis, psoriasis, uveitis, Sjogren's syndrome, and the like.

The polymer-modified IFNα analog proteins can be formulated according to known methods for preparing pharmaceutically useful compositions. Formulations comprising interferons or interferon-like compounds have been previously described (for example, Martin, E. W., In: DISPENSING OF MEDICATION: A PRACTICAL MANUAL ON THE FORMULATION AND DISPENSING OF PHARMACEUTICAL PRODUCTS (Hoover, J. E., Ed.), 8th edition, Mack Publishing Co., Easton, Pa., (1976)). In general, the compositions will be formulated such that an effective amount of the modified interferon-alpha analog is combined with a suitable carrier in order to facilitate effective administration of the composition.

The compositions used in these therapies may also be in a variety of forms, but preferably a form suitable for parenteral administration, such as an injectable or infusible solution. Pharmaceutical compositions suitable for parenteral administration include formulations of the polymer-modified IFNα protein analog with a suitable buffer, e.g., Tris-HCl, acetate or phosphate such as dibasic sodium phosphate/monobasic sodium phosphate buffer, and, optionally, pharmaceutically acceptable excipients, e.g., sucrose, carriers, e.g., humanor recombinant plasma albumin, tonicity agents, e.g. NaCl, preservatives, e.g., thimerosol, cresol or benyl alcohol, and surfactants, e.g., tweens or polysorabates in sterile water for injection. The polymer-modified IFNα protein analog may be stored as a lyophilized powder under a refrigeration, and reconstituted prior to use. Alternatively, aqueous solutions containing the polymer-modified IFNα protein analog may be stored in prefilled, multi-dose syringes such as those useful for delivery of drugs such as insulin. Typical suitable syringes include systems comprising a prefilled vial attached to a pen-type syringe such as the Novolet® Novo Pen available from Novo Nordisk, as well as prefilled, pen-type syringes which allow easy self-injection by the user. Other syringe systems include a pen-type syringe comprising a glass cartridge containing a diluent and lyophilized polymer-modified IFNα protein analog powder in a separate compartment.

A suitable dosage of the modified proteins can be readily determined by a skilled medical provider, based on the known therapeutic dosages for mature IFN-α. Since the IFNα analogs described herein offer a low cytotoxicity, dosages higher that those given for a mature IFN-α are contemplated. In one embodiment, a parenteral dose of the polymer-modified IFNα analog protein that is at least two-fold, preferably three-fold, and still more preferably five-fold, higher that the human dose recommended for currently approved pegylated interferons, such as PEG Intron® and Pegasys®. For example, for treatment of hepatitis C, the currently administered dose of PEG-modified IFNα is 180 μg weekly; a dose of the polymer-modified IFNα analog protein described herein of 360 μg weekly, or 540 μg weekly, preferably 720 μg weekly, or higher is contemplated. In a preferred embodiment, a dose of 900 μg of polymer-modified IFNα analog protein is given weekly, to achieve greater efficacy in producing a sustained viral response in patients, and with less toxicity and better tolerability than found with currently approved therapies PEG-modified IFNα proteins.

In one embodiment, the polymer-modified IFNα analog protein is administered to a patient at a dose and frequency sufficient to achieve a substantially steady state plasma concentration of the protein analog. In this embodiment, the steady state plasma concentration has no substantial cytotoxic effect on hepatocytes, as evidenced by, for example, an in vitro study where hepatocytes are cultured for a selected period of time with a selected concentration of the polymer-modified IFNα analog protein, and metabolism of the hepatocytes is evaluated as an indication of toxicity, similar to the study described in Example 5.

B. Combination Therapies

The interferon compositions described herein may be used in combination with other therapies. For example, for treatment of chronic hepatitis virus infection, the polymer-modified IFNα analog protein can be administered in combination with the synthetic nucleoside Ribavirin.

For the treatment of tumors and other cancers, the polymer-modified IFNα analog protein can be administered in combination with any one or more of the following exemplary antitumor agents: 2-Chlorodeoxyadenosine, 5416 and SU 6688 (both from Sugen, Inc.), 5-flurouracil, 6-Mercaptopurine, 6-Thioguanine, Actinomycin D, Adriamycin, Aldesleukin, Alemtuzumab, Aletretinoin, Allopurinol, Alpha interferon, Altretamine, Amifostine, Aminoglutethimide, Amsacrine, Anagrelide, Anastrozole, anti-EFGR monoclonal antibody ABX (Abgenix), Arsenic trioxide, Aspariginase, Azacitidine, Azacytidine, Azathioprine, BCNU, Bevacizumab, Bexarotene, Bicalutamide, Bleomycin, BMS-247550 (Bristol-Myers Squibb), Busulfan, Camptothecin, Capecitabine, Carboplatin, Carmustine, CCNU, Cetuximab, Chlorambucil, Cisplatin, Cl 1033 (Pfizer Global Research and Development), Cladribine, Clarithromycin, Clodronate, Cyclophosphamide, Cytarabine, Cytosine Arabinoside, Dacarbazine, Dactinomycin, Daunorubicin, Daunorubicin hydrochloride, DC 101 (a KDR VEGF Receptor 2 from ImClone Systems), Decitidine, Denileukin diftotox, Dexamethasone, Dexamethasone acetate, Dexamethasone sodium phosphate, Dexoycoformycin, Dexrazoxane, Docetaxel, DTIC, EMD 72000, Epirubicin, EPO906 (Novartis Pharmaceuticals), Erlotinib, Estramustine phosphate, Ethinyl estradiol, Etoposide, Exemestane, Filgrastim, Floxuridine, Fludarabine, Fludarabine phosphate, Fluoxymesterone, Fluroruracil, Flutamide, Fulvestrant, Gemcitabine, Gemfitinib (Iressa), Gemfitizib, Gemtuzumab ozogamicin, Gleevec, Goserelin, Goserelin acetate, GW 572016 (GlaxoSmithKline), Herceptin, Herzyme (Elan Pharmaceutical Technologies and Ribozyme Pharmaceuticals), Hexamethylmelamine, Hydroxyurea, I-131 Tosotumomab, Ibritumomab, Ibritumomab tiuxetan, Idarubicin, Ifosfamide, Imatinib Mesylate, IMC-1C11 (ImClone Systems), Interleukin-11, interleukin-2, Irinotecan, Isofosfamide, isotretinoin, Ketoconazole, Lenalidomide, Letrozole, Leucovarin, Leucovirin, Leucovorin, Leuprolide, LHRH agonist, Lomustine, Mechlorethamine, Medroxyprogesterone, Megestraol acetate, Megestrol, Melphalan, Melvax II (Imclone Systems and Merck KgaA), Mercaptopurine, Methotrexate, Mithramycin, Mitomycin, Mitomycin C, Mitotane, Mitoxantrone, Mitumomab (Imclone Systems and Merck KGaA), Monoclonal antibody 425 (Merck KGaA), Monoclonal antibody ICR-62 (ICR, Sutton, England), Navelbine, Nelarabine, Neumega (IL-11), Nilutamide, Octreotide, Octreotide acetate, ONTAK (denileukin diftitox), Oxaliplatin, Paclitaxel, Pamidronate, Patnidronate, PC-SPES, Pegaspargase, Pegfilgrastim, Pemetrexed, Pemetrexol, Pentostatin, Pilocarpine hydrochloride, PKI 166 (Novartis), EKB 569 (Wyeth-Ayerst), Plicamycin, Predisolone, Predisone, Procarbazine, Progestins, Raloxifene, Raltitrexol, Rituximab, Samarium-153 lexidronam, Sargramostim, Semustine, Sorafenib, Streptozocin, Sunitinib, Suramin, Targretin, Temozolamide, Teniposide, Testosterone propionate, Thalidomide, TheraCIM-h-R3 (Center of Molecular Immunology), Thioguanine, Thiotepa, Topotecan, Toremifene, Tositumomab, Trastuzmab-maytansinoid conjugate (Genentech, Inc.), Tretinoin, Triptorein pamoate, Triptorelin, Valrubicin, Velcade (burtezomid), Vinblastine, Vincristine, Vinorelbine, and Zoledronic acid.

Similarly, for treatment of tumors and other cancers, the polymer-modified IFNα analog protein can be administered in combination with any one or more of the following exemplary antiviral agents: A-848837, Abacavir, Acyclovir, Adefovir, Amantadine, Azidothymidine, Benzothiazole antiviral compounds, Ciclofovir, Delavirdine, Didanosine, Dideoxycytidine, Efavirenz, Emtricitabine, Enfuvirtide, Entecavir, Famciclovir, Fomivirsen, Foscarnet, Ganciclovir, Gardasil, Idoxuridine, Indinavir, Interferons, Lamivudine, Lobucavir, Lomivudine, Loviride, Nelfinavir, Nevirapine, Oseltamivir phosphate (Tamiflu), Penciclovir, Pleconaril, Pokeweed antiviral protein, Pyrimidine antiviral, Ribavirin, Rimantadine, Ritonavir, Saquinavir, Stavudine, Telbivudine, Tenofovir, Triazine antiviral, Trifluridine, Valacyclovir, Valgancyclovir, Vidarabine, Zalcitabine, Zanamivir, and Zidovudine.

Effective doses and administration schedules for these and other antitumor and antiviral agent are known in the art. Other combinations will be apparent to those skilled in the medical field.

EXAMPLES

The following examples are illustrative in nature and are in no way intended to be limiting.

Example 1

Synthesis of IFNα Analogs and Pegylated-IFNα-N7

A. Preparation of IFNα Protein Analogs Based on Native Human IFNαD

A synthetic gene encoding a human IFNα protein analog, termed HuIFNα-NLV, was constructed by first backtranslating the amino acid sequence of HuIFNα containing 15 interferon-tau (IFNτ) amino acid substitutions within the first 27 N-terminal positions with codon usage optimized for *Pichia pastoris*. The nucleotide sequence was edited to include five restriction sites spaced throughout the length of the construct. The synthetic gene sequence was divided into four nucleotide fragments. The individual fragments, each approximately 150 base pairs in length, were constructed by sequential ligations of oligonucleotides. The fragments were sequentially cloned into the G2 bacterial vector (Operon Technologies, Alameda, Calif.) to yield the gene encoding HuIFNα-N0 (see FIG. 1). The synthetic gene was then cut out of the bacterial vector and ligated into the XhoI/NotI sites of the pPICZ-α vector (Invitrogen, San Diego Calif.) for expression in *Pichia pastoris*. This expression vector construct is called pNLV and is shown in FIG. 2.

The synthetic genes encoding the analogs shown in FIG. 1 and identified as HuIFNα-N1, HuIFNα-N2, HuIFNα-N3, HuIFNα-N6, and HuIFNα-N7 were also constructed by sequential ligations of oligonucleotides. The pNLV construct described above was digested with XbaI and BstEII and annealed oligonucleotides Linker1 (SEQ ID NO:28) and Linker 2 (SEQ ID NO:29) were ligated into these sites to produce an intermediate vector construct. This step removed the nucleotide sequence corresponding to the N-terminal section of HuIFNα-N0. The nucleotide fragments encoding the N-terminal sequence mutations for IFNα-N1, IFNα-N2, IFNα-N3, IFNα-N6 and IFNα-N7 were prepared by sequential ligation of oligonucleotides. The intermediate vector construct was digested with XhoI and EcoRI and the nucleotide fragments were then ligated into the XhoI/EcoRI sites of the intermediate construct to produce analogs HuIFNα-N1, HuIFNα-N2, HuIFNα-N3, HuIFNα-N6, and HuIFNα-N7 in the pPICZ-α vector. Nucleotide sequences for the forward strands and reverse strands for each fragment are given in SEQ ID NOs:30-43.

For expression of the recombinant interferon analogs, the coding sequence of each gene was inserted into the pPICZ-α expression vector (Invitrogen, San Diego, Calif.) using the XhoI and NotI restriction endonuclease sites on the vector. The pPICZ-α expression vector provides a variety of elements to facilitate expression and purification of the recombinant interferons. For example, the vector includes an expression cassette containing the methanol-regulated alcohol oxidase (AOX) promoter. In methanol grown yeast cells, approximately 5% of the polyA+RNA is from the AOX1 gene. In addition, the vector also contains the secretion signal sequence from the *Saccharomyces cerevisiae* α factor prepro peptide which directs the secretion of the protein into the culture medium. The vector also provides selection of recombinant bacteria and yeast cells using the Zeocin antibiotic coded for by the *Sh ble* gene (*Streptoalloteichus hindustanus ble* gene).

The recombinant plasmids encoding HuIFNα analogs were electroporated into the X-33 wild-type *Pichia pastoris* strain for large-scale growth. Recombinant yeast colonies were grown and induced according to the protocols provided by Invitrogen. Supernatants were collected and filtered using a 0.8/0.2 mm pore size acrodisc filter (Gelman Sciences, Ann Arbor, Mich.). These supernatants were concentrated and buffer exchanged with 10 mM Tris, 150 mM NaCl, and concentrated to a final volume of 2 mL with a Centricon Plus-20 (Millipore Corporation, Bedford, Mass.) prior to loading onto a HiPrep Sephacryl 26/60 S-100 High Resolution size exclusion column at 4° C. (Pharmacia, Peapack, N.J.). The majority of the HuIFNα analog proteins were in fraction 3.

B. Preparation of Analogs Based on HuIFNα2b

A similar approach was used to generate the gene and expression vector to produce analogs based on the native human IFNα2b protein, HuIFNα2b. In brief, the gene encoding the analog rHuIFNα2b, designated NLVgα2b, was constructed by first backtranslating the amino acid sequence of HuIFNα2b containing the desired IFNα substitutions at residues 19, 20, 22, 24, and 27 with codon usage optimized for *Pichia pastoris*. Oligonucleotides were synthesized to generate, by sequential ligations, four nucleotide fragments at about 150 base pairs in length. The fragments were sequentially cloned into the G2 bacterial vector (Operon Technologies, Alameda, Calif.) to yield the gene, NLVgα2b. The gene was expressed and purified using the same methods used for the other human IFNα analogs (Example 1A). The sequence for the IFNα2b analog is identified by SEQ ID NO:47 and referred to herein as IFNα2b-N7.

C. Modification of Analogs with Poly(ethylene glycol)

The analog identified herein as IFNα2b-N7 (SEQ ID NO:48), prepared as described in Example 1B, was conjugated with a 40 kDa branched methoxypolyethylene glycol moiety at the N-terminal cysteine by a reductive amination between the analog and mPEG2-butyraldehyde (Nektar Therapeutics, San Carlos, Calif.).

Example 2

In Vitro Antiviral Activity of Pegylated-IFNα2b-N7

The antiviral activity (Units/mL) of IFNα2b-N7 (SEQ ID NO:48) and PEG(40 kDa)-IFNα2b-N7 (PEG modified SEQ ID NO:48, prepared as described in Example 1C) was determined and compared to the antiviral activity of IFN-α2b (Intron A®) and the pegylated IFNα2a product identified by the tradename Pegasys®, using an assay based on the Madin Darby bovine kidney (MDBK) cell line and the vesicular stomatitis virus (VSV) as the challenge virus.

The antiviral potency of the interferons was assessed by testing the protective effect of the interferon on MDBK cells against VSV. Dilutions of the interferons were added to confluent MDBK cell monolayers, grown in 96-well flat bottom plates, and incubated for 18 hrs prior to addition of the virus challenge. Recombinant human IFN-αA (Biosource International, Camarillo, Calif.) was used as the standard interferon control for the assay. Dilutions of each interferon sample were assayed to obtain the point at which fifty percent of the MDBK cells were protected from VSV infection. Percent protection was calculated using the following formula:

AVERAGE($A_{450-630}$ Test Well−AVERAGE($A_{450-630}$ Virus Control Wells))×100/Average($A_{450-630}$ Untreated Cell Control Wells)

Where $A_{450-630}$ is the absorbance at 450-630 nm.

One antiviral unit is defined as 50% protection. The product potency unit is expressed as units per milligram (U/mg). The results are shown in Table 1. IFNα2b (Intron A®) and IFNα2b-N7 demonstrate similar antiviral potencies with specific activities at ~$10^9$ U/mg. Addition of a 40 kDa PEG moiety to the interferon molecule led to a 10-fold decrease in the in vitro antiviral specific activity, as seen for the pegylated IFNα product identified by the tradename Pegasys® and for PEG(40 kDa)-IFNα2b-N7. Thus, the MDBK/VSV antiviral assay demonstrates that PEG(40 kDa)-IFNα2b-N7 has comparable antiviral activity to the pegylated IFNα product Pegasys®. The pegylated interferon products demonstrated lower in vitro antiviral activity compared to the non-pegylated interferons.

TABLE 1

Comparison of the interferon antiviral specific activity in Madin Darby bovine kidney (MDBK) cell line challenged with vesicular stomatitis virus (VSV)

| Interferon | Specific Activity (U/mg) |
| --- | --- |
| Recombinant human interferon-alpha-A | $6.02 \times 10^8$ |
| Interferon-α2b (Intron-A ®) | $1.09 \times 10^9$ |
| PEG(40 kDa)-IFNα2b-N7 (SEQ ID NO: 48) | $8.43 \times 10^8$ |
| PEG (40 kDa)-IFNα2a (Pegasys ®) | $9.7 \times 10^7$ |
| PEG(40 kDa)-IFNα2b-N7 (PEG-modified SEQ ID NO: 48) | $9.0 \times 10^7$ |

Example 3

In Vitro Antiproliferative Activity of Pegylated-IFNα2b-N7

The in vitro anti-proliferative activity of PEG(40 kDa)-IFNα2b-N7, prepared as described in Example 1C, was compared with the anti-proliferative activity of the pegylated IFNα product identified by the tradename Pegasys®. Seven human tumor cell lines representing major neoplastic categories were cultured and treated with the interferons. The magnitude of cell proliferation was measured by the reduction of the tetrazolium salt WST-1. The degree of reduction of WST-1 of the interferon treated cells was compared to non-treated control cells.

The results are shown in Table 2. The anti-proliferative activity of PEG(40 kDa)-IFNα2b-N7 and Pegasys® were similar in the seven cell lines tested.

TABLE 2

Comparison of interferon anti-proliferative activity in human tumor cell lines[a]

| Cell Line | Cell Line Origin | PEG-IFNα2b-N7 | Pegasys ® |
| --- | --- | --- | --- |
| ACHN CRL-1611 | Renal cell adenocarcinoma | 48 +/− 4 | 42 +/− 3 |
| DLD-1 CCL-221 | Colorectal adenocarcinoma | 72 +/− 7 | 63 +/− 2 |
| HCC1954 CRL-2338 | Breast ductal carcinoma | 72 +/− 12 | 42 +/− 3 |
| HL60 CCL-240 | Acute promyelocytic leukemia | 81 +/− 2 | 75 +/− 4 |
| HUT78 TIB-161 | T-lymphoblast lymphoma | 48 +/− 2 | 32 +/− 1 |
| MCF-7 HTB-22 | Breast epithelial adenocarcinoma | 81 +/− 4 | 74 +/− 3 |
| THP-1 TIB-202 | Acute monocytic leukemia | 85 +/− 7 | 71 +/− 3 |

[a]The mean percent cell line proliferation relative to non-treated control cells is presented for the interferons tested at 1 μg per ml for the representative tumor cell lines. Non-treated controls = 100%, n = 3 for each condition; error is presented as standard error of the mean (SEM).

Example 4

In Vitro Toxicity of Pegylated-IFNα2b-N7

IFNα2b (Intron A®), IFNα2b-N7 (SEQ ID NO:48), PEG-modified IFNα2b-N7, and the pegylated IFNα product identified by the tradename Pegasys® Interferons (Table 4.1.2.A.) were assessed for toxicity as measured by the level of apoptosis in human PBMCs. Human PBMCs were isolated from buffy coat collected from 17 volunteer donors. Interferon concentrations tested ranged from 0.01 μg to 1 μg per mL for IFNα2b-N7 (SEQ ID NO:48) and Intron-A®, and 0.025 μg to 9 μg per mL for PEG(40 kDa)-IFNα2b-N7 and Pegasys®. The PBMCs were cultured with the interferons in wells of 24-well plates at a density of 1.5×10⁶ cells per well. At day 12 of culture, cells were stained with annexin V and propidium iodide, and analyzed for apoptosis by flow cytometry.

The relative levels of toxicity of IFNα2b-N7 (SEQ ID NO:48), PEG(40 kDa)-IFNα2b-N7, Intron-A® and Pegasys® were measured by the induction of apoptosis in human PBMCs, compared to non-treated controls, and expressed as the mean percent specific cell death.

Figure 4A:
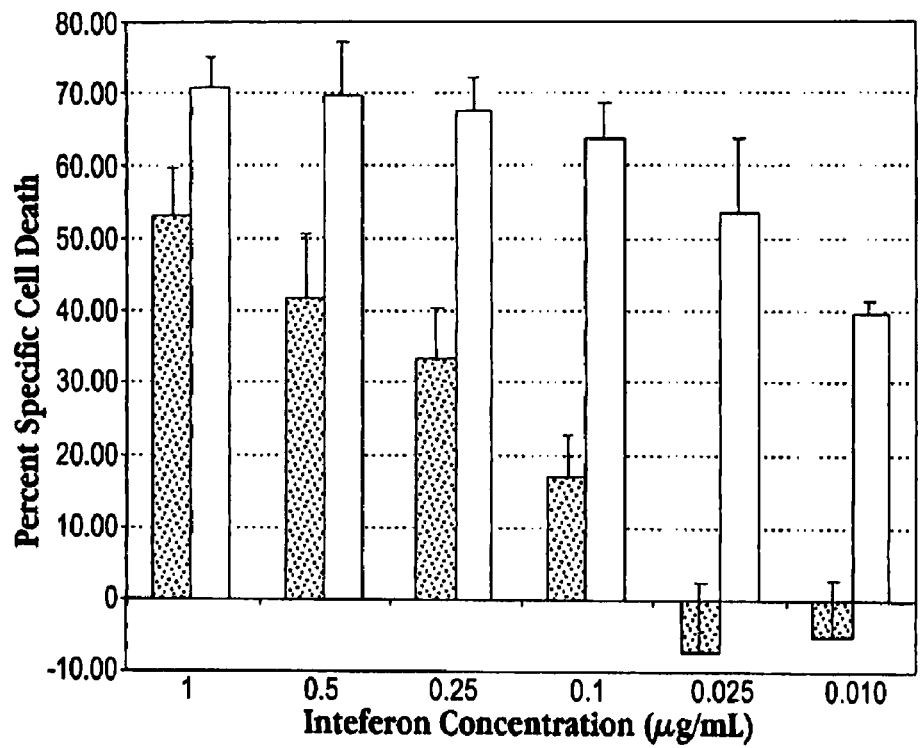
FIGS. 4A-4B are bar graphs showing the percent specific cell death of human peripheral blood mononuclear cells cultured with IFNα2b (Intron A®, open bars, FIG. 4A) or the IFNα analog IFNα2b-N7 (dotted bars, FIG. 4A), or IFNα2b-N7-PEG(40 kDa) (dotted bars, FIG. 4B) or IFNα2a-PEG(40 kDa) (Pegasys®, open bars, FIG. 4B) at the noted concentrations.

The mean percent specific cell death induced in PBMCs by IFNα2b-N7 (SEQ ID NO:48) and Intron-A® at interferon concentrations from 0.01 μg to 1.0 μg per mL cell culture medium is shown in FIG. 4. The results show that IFNα2b-N7 (SEQ ID NO:48) had no apparent toxic effect on PBMCs at concentrations at and below 0.025 μg per mL in contrast to Intron-A®, where at the lowest concentration tested, 0.01 μg per mL, induced apoptosis in 40% of cells. At 0.025 μg per mL no toxicity was detected in the IFNα2b-N7 (SEQ ID NO:48) treated PBMC cultures while a mean percent cell death of 53% was detected in the Intron-A® cultures ($p<0.001$, student T-test). IFNα2b-N7 (SEQ ID NO:48), at the highest concentration tested of 1 μg per mL, remained significantly less toxic compared to Intron-A®, 53% versus 71% mean percent specific cell death ($p=0.015$, student T-test). However, the maximum serum concentration of Intron A® after subcutaneous or intramuscular injection in human patients at the recommended doses ranges from ~0.1 to 1.0 ng/ml. At 500 times higher than the recommended doses for Intron A®, IFNα2b-N7 (SEQ ID NO:48) is still less toxic than Intron A® at its recommended dose.

Figure 4B:
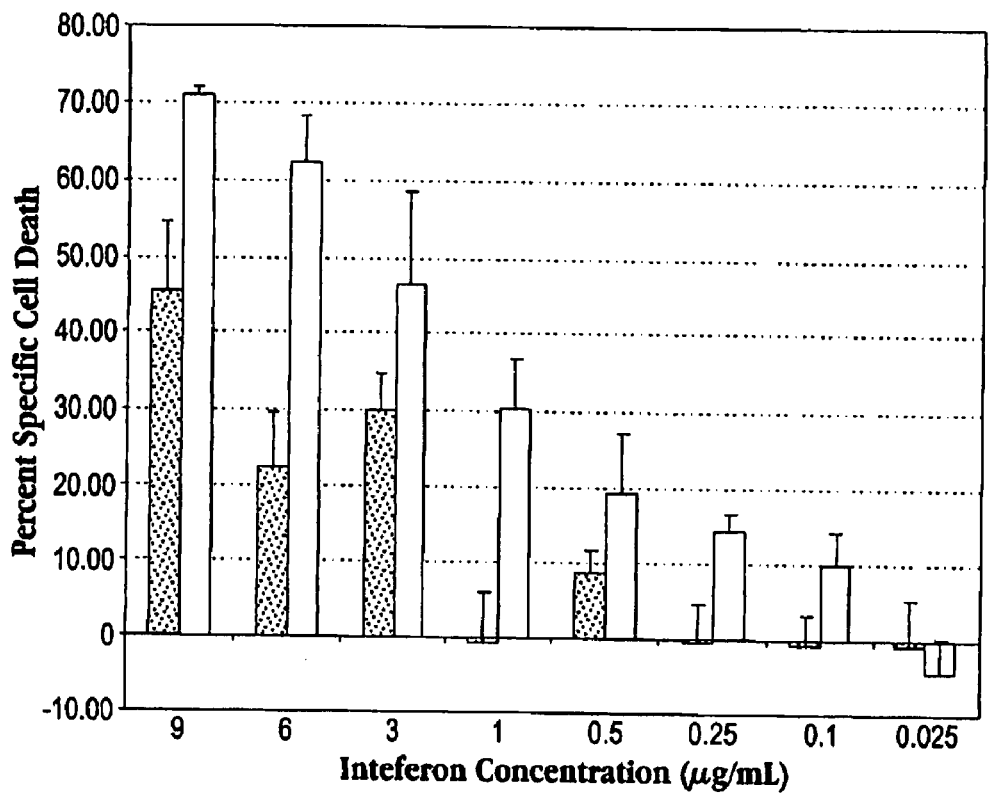

Consistent with the lower toxicity of IFNα2b-N7 (SEQ ID NO-48) compared to Intron-A®, PEG modified IFNα2b-N7 (SEQ ID NO:48) demonstrated significantly less toxicity as measured by the induction of apoptosis compared to Pegasys®, as seen in FIG. 4B. At 1 μg per mL, PEG(40 kDa)-IFNα2b-N7 had a mean percent specific cell death of approximately 0% whereas Pegasys® had a 30% mean specific cell death compared to controls ($p<0.001$, student T-test). The maximum serum concentration of Pegasys® is ~0.025 μg/ml at its recommended dose. PEG(40 kDa)-IFNα2b-N7 showed no toxicity up to 10 times higher than the estimated serum concentration that is reached by the recommended dose of Pegasys® (180 μg/dose).

The data from this study clearly demonstrate that PEG(40 kDa)-IFNα2b-N7 mediates substantially lower toxicity as measured by the induction of apoptosis compared to their commercial counterpart interferons, Intron-A® and Pegasys®. Since both Pegasys® and PEG(40 kDa)-IFNα2b-N7 have 40 kDa PEG moieties attached to the native interferon molecule, the difference in the toxicity profiles stems from five amino acid changes within the PEG(40 kDa)-IFNα2b-N7 molecule. This data supports a five fold higher dose of PEG(40 kDa)-IFNα2b-N7 than the recommended dose of Pegasys®.

Example 5

In Vitro Toxicity of Pegylated-IFNα2b-N7 in Human Hepatocytes

Liver toxicity is another potential therapy limiting adverse side-effect of interferon treatment for Hepatitis C, as well as for cancer therapy. IFNα associated hepatotoxicity in patients is often related to dosage levels, and is detected through rising transaminases. A study was conducted to evaluate the toxicity of IFNα and IFNα analogs in hepatocytes.

Primary human hepatocytes were cultured in matrigel in a 96-well plate format, and treated with IFNα2b-N7 (SEQ ID NO:48) or with Intron-A®, from 0.0001 μg to 1 μg per mL, and with PEG(40 kDa)-IFNα2b-N7 or with Pegasys® from 0.010 μg to 10 μg per mL of hepatocyte culture medium. At day 7 of the cultures, the relative degree of cell metabolism was determined by the reduction of the tetrazolium salt WST-1 as a marker for interferon mediated hepatocyte toxicity, and compared to non-treated control cells.

Figure 5A:
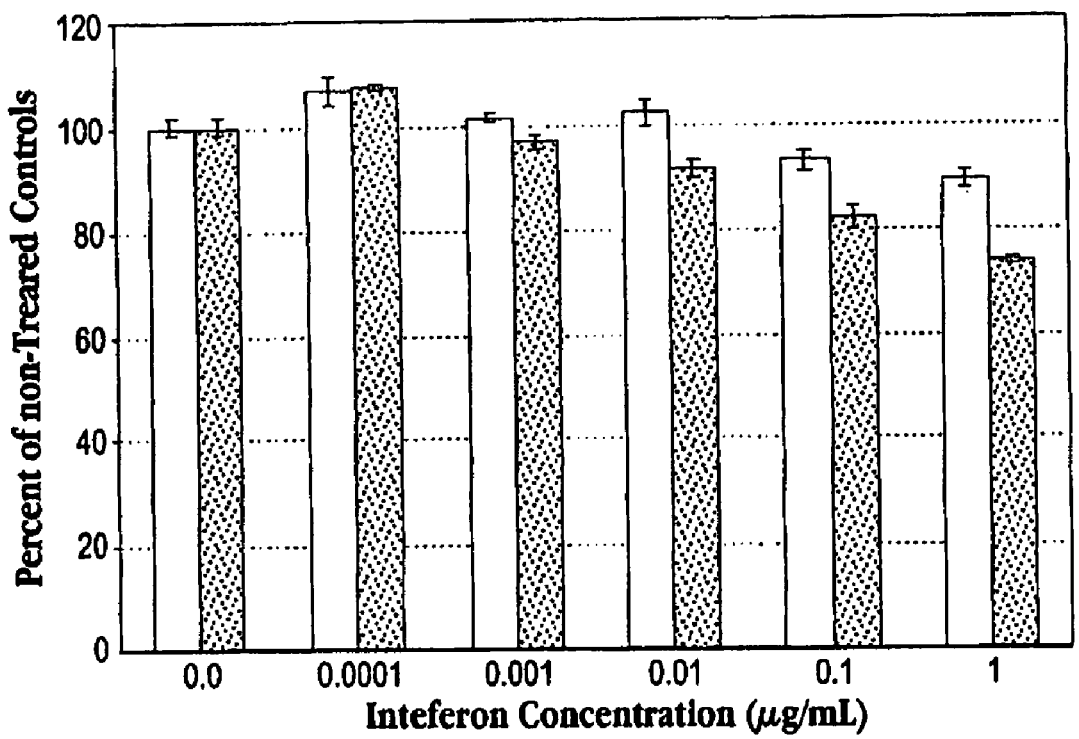
FIGS. 5A-5B shows the effect of IFNα2b-N7 (SEQ ID NO:48, dotted bars) and IFNα2b (Intron A®, open bars) (FIG. 5A) and of PEG(40 kDa)-IFNα2b-N7 (dotted bars) and IFNα2a-PEG(40 kDa) (Pegasys®, open bars) (FIG. 5B) on primary human hepatocytes cultured for seven days in the presence of the interferon before measuring metabolic activity.
Figure 5B:
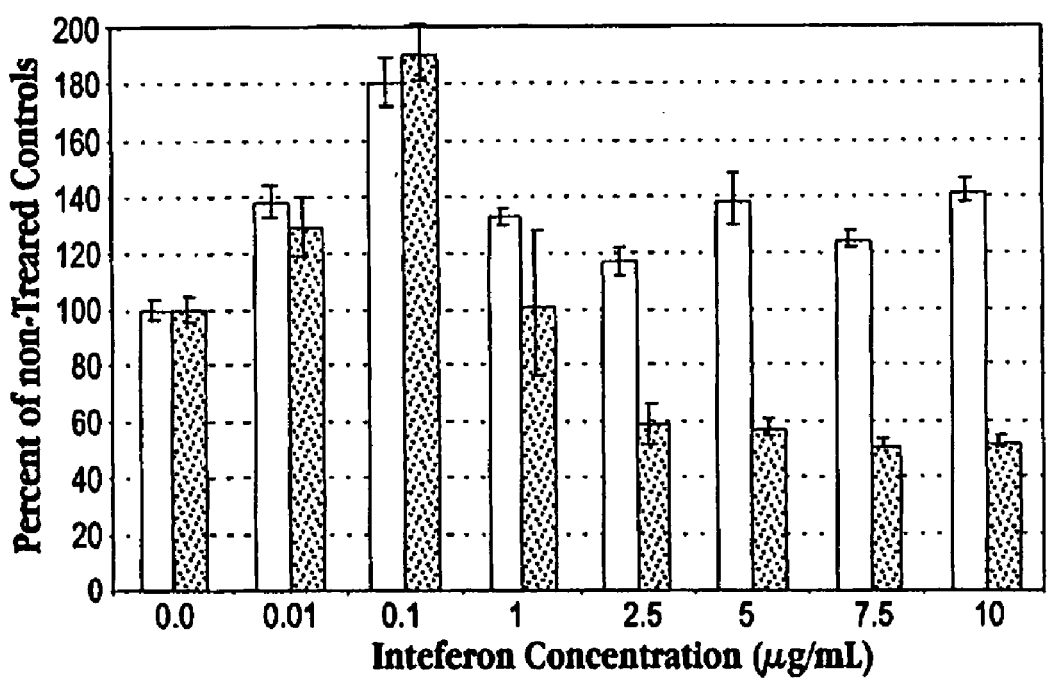

Results are shown in FIGS. 5A-5B. The primary human hepatocytes treated with IFNα2b-N7 showed no negative effect on cell metabolism at and below 0.01 μg per mL of medium at day 7 of culture. This contrasts with Intron-A® which mediated reduced hepatocyte metabolism at a concentration of 0.01 μg per mL culture medium ($p=0.02$, student T-test). At the interferon concentrations of 0.1 μg and 1 μg per mL, IFNα2b-N7 treated hepatocytes showed a 7.3% (+/−2.1 SEM) and a 10.9% (+/−1.8 SEM) reduction in metabolism, respectively. This contrasts with the significantly greater negative effect of Intron-A® on hepatocytes that showed at 0.1 μg per mL an 18.3% (+/−2.71 SEM) reduction in metabolism, and at 1 μg per mL showed a 26.5% (+/−0.7 SEM) reduction in metabolism. At 0.1 μg and 1 μg per mL, Intron-A® had a greater than 2 fold negative effect on hepatocyte metabolism compared to IFNα2b-N7 ($p=0.05$, student T-test).

With respect to FIG. 5B, primary human hepatocytes treated with PEG(40 kDa)-IFNα2b-N7 and Pegasys® showed no toxic effect up to 1 μg per mL. Notably, there appeared to be a protective effect mediated equally by both interferons at 0.01 μg and 1 μg per mL, and for PEG(40 kDa)-IFNα2b-N7 up to 10 μg per mL, on hepatocytes that resulted in a higher metabolic readout compared to controls at day 7. However, above 1 μg per mL, Pegasys® clearly showed significant toxicity as measured by reduced hepatocyte metabolism, from 40% at 2.5 μg ($p<0.001$, student T-test) and 5 μg per mL ($p<0.002$, student T-test), to 50% at 7.5 μg mL ($p<1.3\times10^{-5}$, student T-test) and 10 μg per mL ($p<1\times10^{-4}$, student T-test).

Thus, the results of this study clearly show that both IFNα2b-N7 and PEG(40 kDa)-IFNα2b-N7 have substantially reduced toxicity profiles compared to Intron-A® and Pegasys® in primary human hepatocytes. Intron-A® negatively affected hepatocytes at a level 10 times lower than IFNα2b-N7 (0.01 μg per mL compared to 0.1 μg per mL), while PEG(40 kDa)-IFNα2b-N7 showed no apparent significant negative effect on the hepatocytes at any concentration tested. In contrast, Pegasys® showed significant toxicity on hepatocytes at concentrations at and above 2.5 μg per mL.

Example 6

In Vivo Pharmacokinetics of Pegylated-IFNα2b-N7

The serum elimination profile of PEG(40 kDa)-IFNα2b-N7, prepared as described in Example 1C, in mice after a single dose of $10^7$ U/Kg administered subcutaneously (s.c.) was determined. The serum elimination curve for PEG(40 kDa)-IFNα2b-N7 was compared to the elimination curve for the pegylated IFNα product Pegasys®, also dosed at $10^7$ U/Kg, to determine the difference in absorption and clearance. In addition, end of study serum concentrations of PEG (40 kDa)-IFNα2b-N7 after multiple weekly and biweekly injections were also determined.

PEG(40 kDa)-IFNα2b-N7 and Pegasys® were diluted to the appropriate concentration using sterile PBS and prepared on day of dosing. Each animal was weighed, lightly anesthetized with isoflurane, and administered the test article s.c. at $10^7$ U/Kg. Two mice per test article group per time point were euthanized at predetermined times by $CO_2$ asphyxiation. Blood was collected shortly thereafter by intra-cardiac bleed. Blood samples were spun at 10,000 for 3 minutes and serum was collected. Serum samples were stored at −80° C. until analysis. Estimation of elimination rates at different time periods were determined using Microsoft Excel's Linear Curving Fitting Program. The slope for each liner curve fit was used as an estimate of the elimination rate (ng/mL/h).

All serum samples were assayed using the Human Interferon Alpha ELISA Kit manufactured by Bender Medsystems (CAT# BMS216). The protocol was modified to analyze PEGylated interferons.

Figure 6:
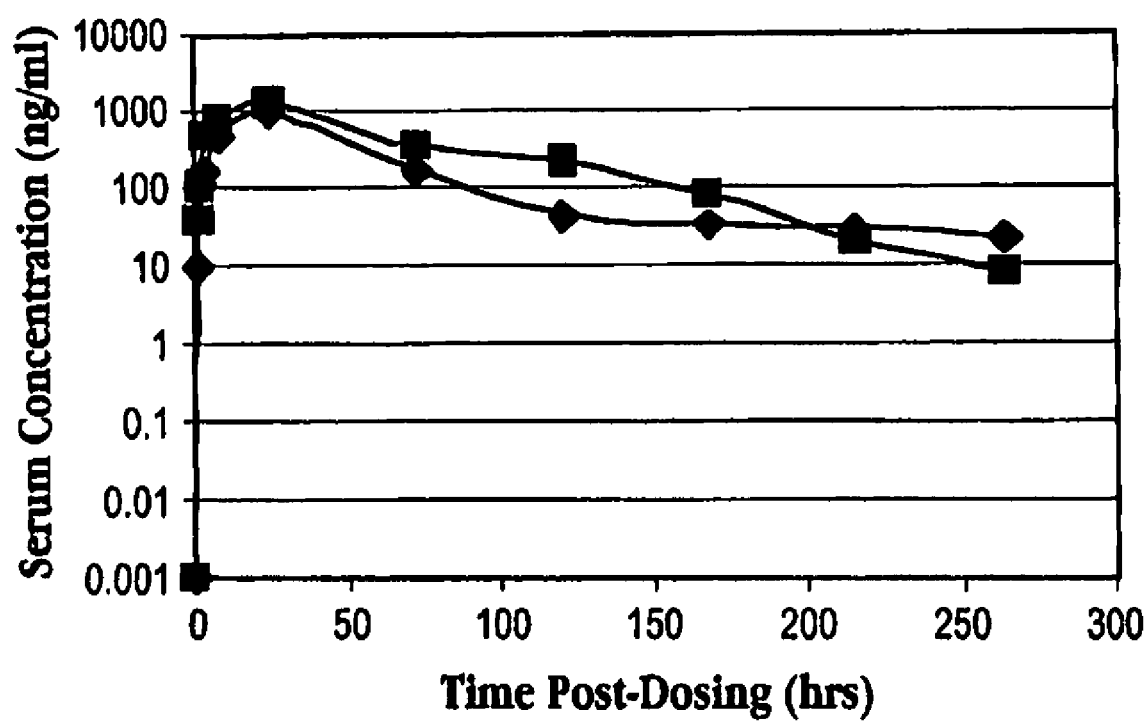
FIG. 6 shows the serum concentration, in ng/mL, as a function of time post dosing, in hours, of mice with PEG(40 kDa)-IFNα2b-N7 (squares) or with IFNα2a-PEG(40 kDa) (Pegasys®, diamonds) at a dose of $10^7$ U/kg.

The results are shown in FIG. 6. Substantial serum levels of PEG(40 kDa)-IFNα2b-N7 (squares) were detectable as early as 1 hour post administration (~10.26 ng/mL). Maximum serum concentration was reached at 24 hrs (~1000.00 ng/mL), after which there was a steady decline in interferon concentration. The estimated elimination rate during the period t=24-72 hours was ~13.83 ng/mL/hr, at which time the serum concentration at 72 hrs had decreased to 339.38 ng/mL (~33.84% of max serum concentration). During the period t=72-216 hours the elimination rate decreased to 2.27 ng/mL/hr, at which time the serum concentration at 168 hrs (7 days) was 79.98 ng/mL (~7.97% of max concentration). Substantial serum levels of PEG(40 kDa)-IFNα2b-N7 were still measurable at 264 hrs (11 days at ~8 ng/ml) and at 384 hrs (14 days at ~1 ng/ml, data not shown). While the serum elimination profile at $10^7$ U/Kg for PEG(40 kDa)-IFNα2b-N7 was very similar to Pegasys® (diamonds, FIG. 5) at $10^7$ U/Kg, Pegasys® cannot maintain high serum concentrations beyond the maximum serum concentrations reached by its recommended dose, which is five times less than the human equivalent dose of $10^7$ U/Kg, due to its toxicity.

Example 6

In Vivo Antiproliferative Activity of Pegylated-IFNα2b-N7

The antitumor (antiproliferative) effect of IFNα2b-N7 (SEQ ID NO:48) and of PEG(40 kDa)-IFNα2b-N7 was evaluated using a nude mouse xenograft model for human renal cell carcinoma. The anti-tumor effects were compared to xenografts treated with phosphate buffered saline (PBS) or with two commercially available IFNα products, Intron A® and Pegasys®, under similar study conditions.

Female nude mice were implanted with a renal carcinoma cell line (ACHN) at $5\times10^6$ cells/200 μL s.c. on the right flank. The ACHN cell line (ATCC CRL-1611) is derived from a malignant renal adenocarcinoma. Treatment was started on the day of xenograft implantation. Mice were dosed with PBS (10 mL/kg), PEG(40 kDa)-IFNα2b-N7, or Pegasys® ($10^6$ or $10^7$ U/kg) once weekly. Another set of mice were dosed with PBS (10 mL/Kg), IFNα2b-N7 (SEQ ID NO:48), or Intron A® ($10^6$ or $10^7$ U/Kg) three times per week. Tumors were measured using a digital caliper. Two measurements were taken twice a week for each tumor to determine tumor volume and tumor ellipse area. Mice were sacrificed 28 days after xenograft implantation. Log normal transformation of tumor volume and area measure was used to normalize data and reduce the skewing of data by outliers. Area under the curve (AUC) was used to compare treatment effects. Analysis of variance (ANOVA) was used to determine statistical significance ($p \leq 0.05$) of treatment effect. ANOVA was followed by student t-Test: Two-Sample Assuming Unequal Variances to compare significance ($p \leq 0.05$) of test article treatment to PBS treatment.

Figure 7A:
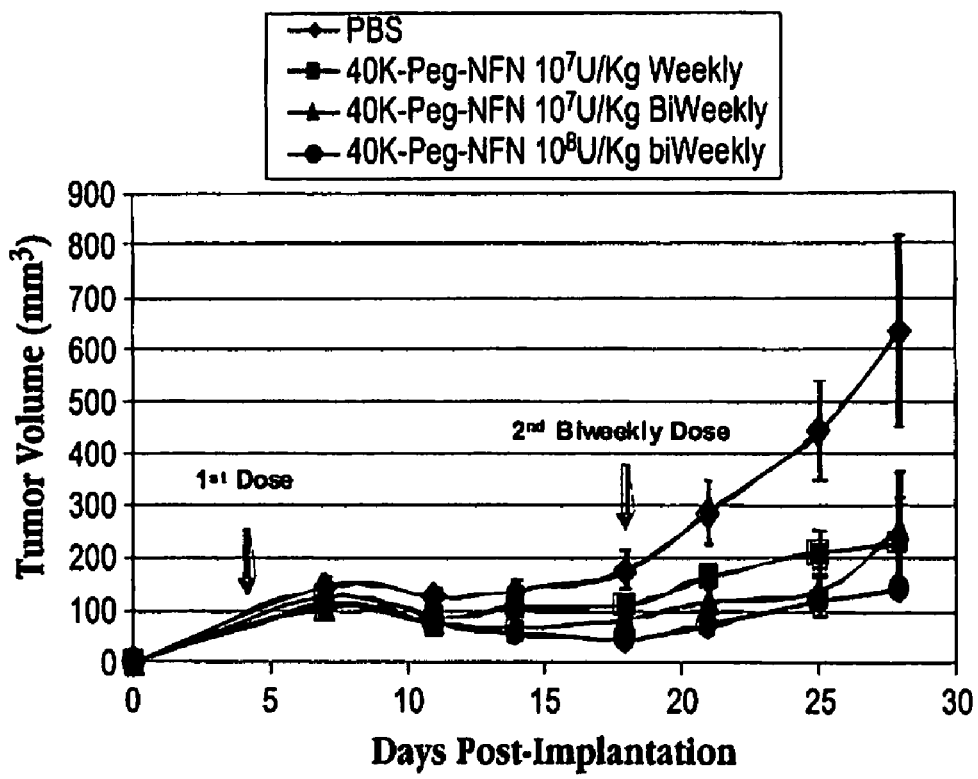
FIG. 7A shows the area under the curve for tumor volume measurements from nude mice implanted with renal carcinoma cells and dosed with the IFNα protein analog IFNα2b-N7 (SEQ ID NO:48) ($10^6$ and $10^7$ U/Kg) or Intron A® ($10^6$ and $10^7$ U/Kg) thrice weekly for 28 days starting on day of implantation.
Figure 7B:
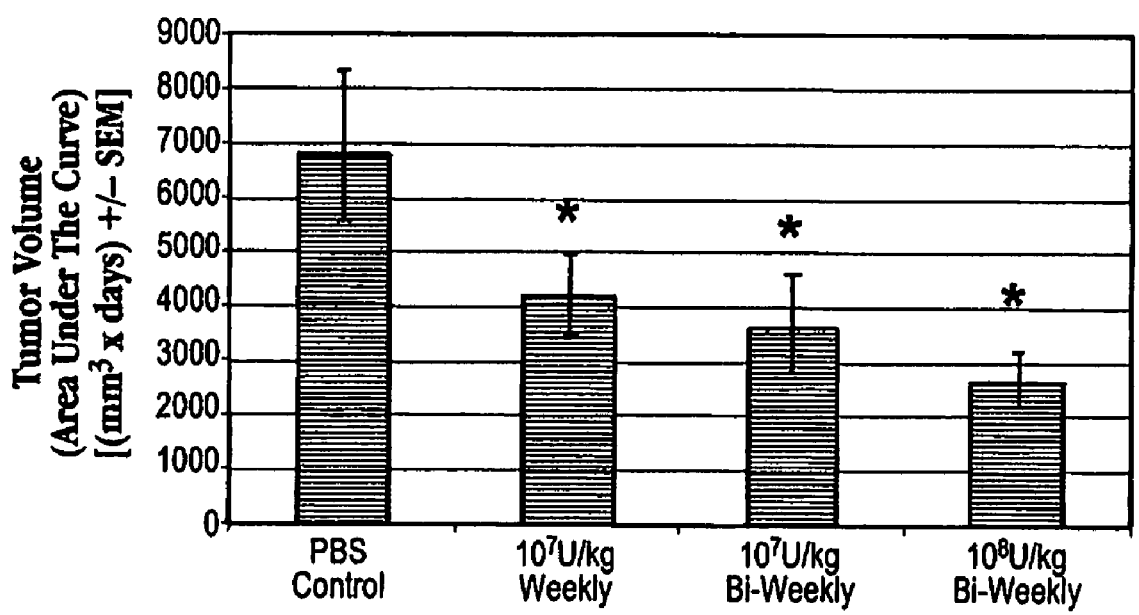
FIG. 7B shows the area under the curve for tumor volume measurements from nude mice implanted with renal carcinoma cells and dosed with PEG(40 kDa)-IFNα2b-N7 (SEQ ID NO:48) ($10^6$ and $10^7$ U/Kg) or Pegasys® ($10^6$ and $10^7$ U/Kg) weekly for 28 days starting on the day of implantation.

The results are shown in FIGS. 7A-7B. The average tumor volume and area was ~200 $mm^3$ and 30 $mm^2$, respectively, in all the groups at 7 days post implantation. Drug effect on tumor growth became evident after 7 days post implantation. IFNα2b-N7 (SEQ ID NO:48), PEG(40 kDa)-IFNα2b-N7, and Pegasys® dosed at $10^7$ U/kg significantly inhibited tumor growth. Treatment with PEG(40 kDa)-IFNα2b-N7 and Pegasys® at $10^6$ U/Kg showed moderate tumor growth inhibition but was not statistically significant. Animals treated with Intron A® dosed three times per week, showed some level of inhibition of tumor growth between days 11 and 21 post-implantation. However, by day 21 Intron A® treated mice demonstrated reduced treatment effect which resulted in no significant difference in tumor volume and area compared to PBS treated animals at the end of study, as seen in FIG. 7A.

A dose of $10^7$ U/Kg in mice converts to a human equivalent dose (HED) of 840 μg/dose, which is approximately five times the recommended human dose for Pegasys® (180 μg/dose). Pegasys® cannot be dosed at such a high concentration due to its toxic effects, however, such a dose of pegylated-IFNα2b-N7 is not accompanied by treatment—limiting adverse events.

Example 7

In Vivo Potency of Pegylated-IFNα2b-N7

The efficacy of PEG(40 kDa)-IFNα2b-N7 was tested for anti-tumor efficacy on a nude mouse xenograft model for human breast cancer. Comparison of weekly and bi-weekly drug dosing intervals was also determined for PEG(40 kDa)-IFNα2b-N7 in this model.

Female nude mice were implanted with a breast ductal carcinoma cell line (HCC1954) at $5\times10^6$ cells/200 μL SC on the right flank. The HCC1954 cell line (ATCC CRL-2338) is derived from a primary stage invasive ductal carcinoma with no lymph node metastasis. Treatment was started on day 4 post xenograft implantation. Test subjects were dosed with PBS (10 mL/Kg), PEG(40 kDa)-IFNα2b-N7 at $10^7$ U/Kg (weekly or biweekly) or PEG(40 kDa)-IFNα2b-N7 at $10^8$ U/Kg biweekly. Tumors were measured using a digital caliper. Two measurements were taken twice a week for each tumor to determine tumor volume. Geometric mean for tumor volume measures was used to normalize data and reduce the skewing of data by outliers. Microsoft Excel linear regression curve fitting program was used to determine linear growth rates (slope) for each of the tumor growth curves. Area under the curve (AUC) was determined using the trapezoid method and log normal transformed data was used for statistical analysis and to compare treatment effects. At end of study (28 days post xenograft implantation) test subjects were euthanized. Analysis of variance (ANOVA) was used to determine statistical significance ($p \leq 0.05$) of treatment effect. ANOVA was followed by student t-Test: Two-Sample Assuming Unequal Variances to compare significance ($p \leq 0.05$) of test article treatment to PBS treatment.

Figure 8A:
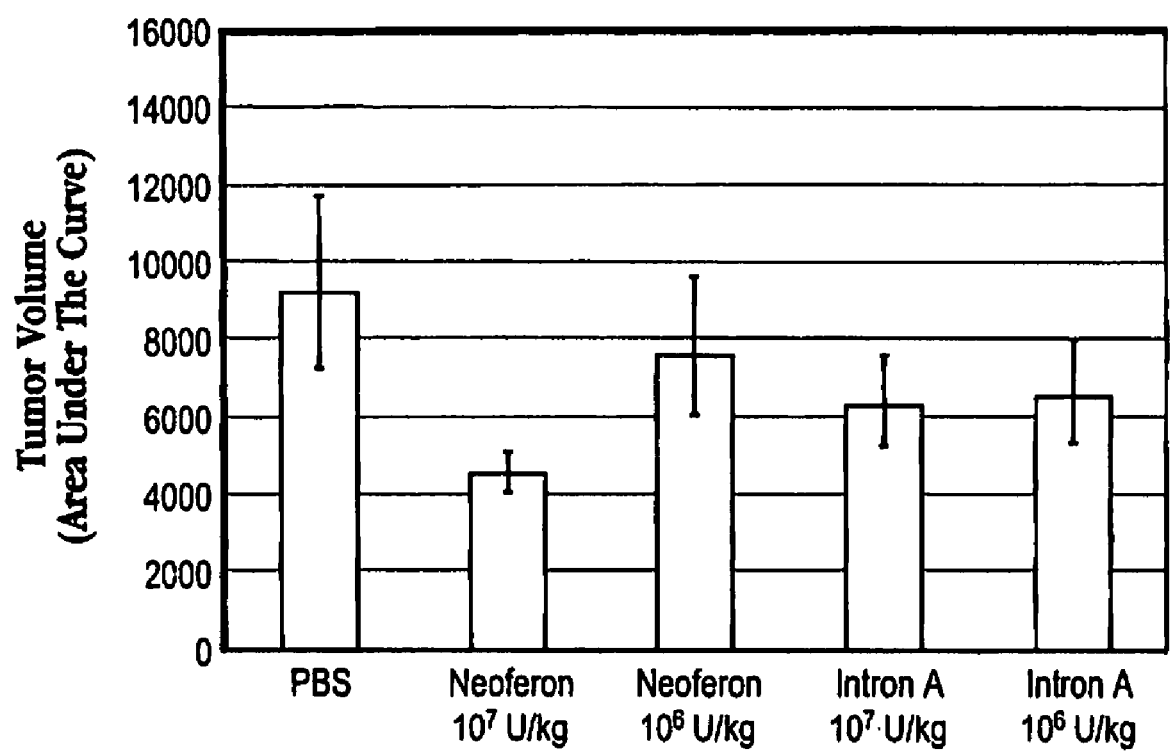
FIG. 8A shows the tumor volume, in $mm^3$, of mice bearing a human breast carcinoma tumor xenograft, as a function of time, in days, post treatment with saline (diamonds), PEG(40 kDa)-IFNα2b-N7 dosed at $10^7$ U/kg weekly (squares), PEG (40 kDa)-IFNα2b-N7 dosed at $10^7$ U/kg biweekly (triangles), and PEG(40 kDa)-IFNα2b-N7 dosed at $10^8$ U/kg biweekly (circles).
Figure 8B:
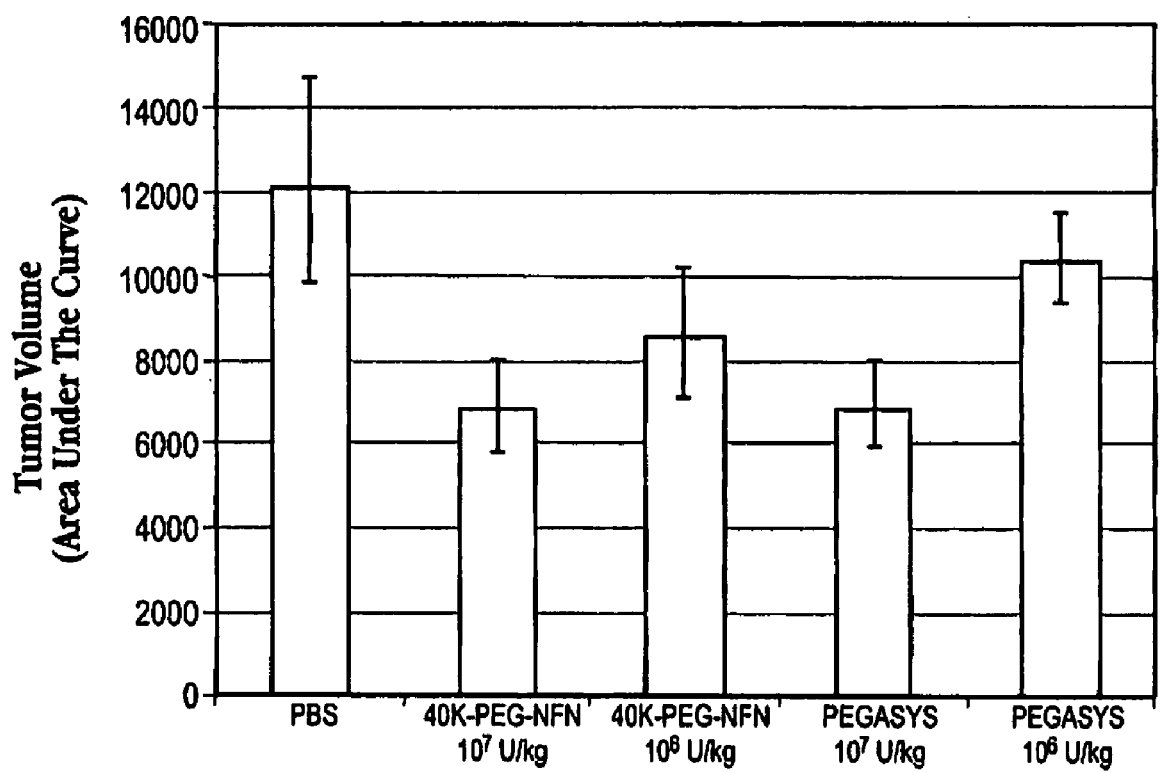
FIG. 8B is a bar graph showing the area under the curve for tumor volume measurements from nude mice implanted with primary mammary gland ductal carcinoma cells (HCC1954) and dosed with PEG(40 kDa)-IFNα2b-N[7] ($10^7$ and $10^8$ U/kg) biweekly or ($10^7$ U/kg) weekly for 28 days starting on day 4 of post-implantation.

The results are shown in FIGS. 8A-8B. Drug treatment effect on tumor volume was observed at the first measurement on day 7 post xenograft implantation. The average tumor volume at first measurement for PBS (diamonds, FIG. 8A), PEG(40 kDa)-IFNα2b-N7 dosed at $10^7$ U/kg weekly (squares), PEG(40 kDa)-IFNα2b-N7 dosed at $10^7$ U/kg biweekly (triangles), and PEG(40 kDa)-IFNα2b-N7 dosed at $10^8$ U/kg biweekly (circles) treatment was ~144±15.00, 122±14.00, 103±7.33 and 110±15.41 mm$^3$, respectively. Significant tumor growth inhibition was noted throughout the study for all dose groups and dose intervals using PEG(40 kDa)-IFNα2b-N7.

Tumor growth rate for PEG(40 kDa)-IFNα2b-N7 dosed at $10^7$ U/kg weekly, PEG(40 kDa)-IFNα2b-N7 dosed at $10^7$ U/kg biweekly and PEG(40 kDa)-IFNα2b-N7 dosed at $10^8$ U/kg biweekly (5.27, 3.614 and 3.614 mm$^3$/day, respectively), was slightly slower than that for the PBS control group (8.63 mm$^3$/day) during the period t=0-18 days as determined by the slope of each tumor growth curve. However, during the period t=18-28 days, tumor growth rates for treated test subjects were significantly reduced compared to PBS treatment (PEG(40 kDa)-IFNα2b-N7 at $10^7$ U/kg weekly: 7.3 mm$^3$/day; PEG(40 kDa)-IFNα2b-N7 at $10^7$ U/Kg biweekly: 12.67 mm$^3$/day; PEG(40 kDa)-IFNα2b-N7 at $10^8$ U/Kg biweekly: 7.91 mm$^3$/day; and PBS 39.64 mm$^3$/day).

Analysis of AUC for tumor volume for test subjects treated with PEG(40 kDa)-IFNα2b-N7 dosed at $10^7$ U/kg weekly, PEG(40 kDa)-IFNα2b-N7 dosed at $10^7$ U/kg biweekly and PEG(40 kDa)-IFNα2b-N7 dosed at $10^8$ U/kg biweekly shows a statistically significant effect on tumor growth (38.85, 47.07 and 61.27% inhibition, respectively) when compared to PBS treatment.

Example 8

In Vivo Treatment of Viral Infections with Pegylated-IFNα2b-N7

Syrian golden hamster are highly susceptible to encephalomyocarditis virus (EMCV) and herpes simplex virus (HSV) infection. Therefore, EMCV and HSV were chosen for hamster challenge studies to evaluate the antiviral effects of IFNαs in vivo.

Syrian golden hamsters (female; 6-8 weeks old; weight 65-75 g; Charles River Breeding Laboratories) are injected i.p. (300 μL) with 1×10$^3$ PFU and 3×10$^3$ PFU of EMCV. 6 hours prior to EMCV injection the following doses of IFNα2b-N7, PEG(40 kDa)-IFNα2b-N7, rHuIFNα2b, or PEG-HuIFNα2b are injected i.p. per hamster: $10^4$ U, $10^5$ U, $10^6$ U, and $10^7$ U. PBS is injected i.p. as control. Five hamsters are in each of the five test groups.

In another group of test animals, the Syrian hamsters (female; weight 65-75 g; Charles River Breeding Laboratories) receive an i.p. virus inoculum of 300 μL of HSV-2 containing $10^4$ TCID$_{50}$/ml which will result in mean survival time of 5 days. Doses of $10^5$, $10^6$, and $10^7$ Units of IFNα2b-N7, PEG (40 kDa)-IFNα2b-N7, rHuIFNα2b, or PEG-HuIFNα2b are administered i.p. in a single dose at −6 or 10 hours relative to infection. PBS is injected i.p. as control. Ten hamsters are in each of the five test groups.

The survival time of infected hamsters is determined from daily records. Significance of differences in survival time between treatments is assessed by the log-rank chi-square method.

The survival time of the animals treated with PEG(40 kDa)-IFNα2b-N7 is longer than the other test animals.

Example 9

In Vivo Treatment of Hepatitis C with Pegylated-IFNα-N7

Twenty-four human subjects diagnosed with Hepatitis C are assigned to four treatment groups. Patients in group 1 are treated with 90 μg PEG(40 kDa)-IFNα2b-N7; patients in group 2 are treated with 180 μg PEG(40 kDa)-IFNα2b-N7; patients in group 3 are treated with 450 μg PEG(40 kDa)-IFNα2b-N7; and patients in group 4 are treated with 90 μg PEG(40 kDa)-IFNα2b-N7. The patients receive the noted dose weekly for four weeks. During the test period, and for four weeks after treatment, blood samples are drawn to measure alanine amino transferase as a biomarker for treatment of the hepatitis C infection.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A composition, comprising
   a protein comprising the amino acid sequence set forth in SEQ ID NO:48, wherein said protein is covalently attached to at least one hydrophilic polymeric chain to form a conjugate having a reduced cellular toxicity compared to the protein of SEQ ID NO:48 not covalently attached to at least one hydrophilic polymeric chain, and
   an antitumor or an antiviral agent.

2. The composition of claim 1, wherein said hydrophilic polymeric chain is polyethylene glycol.

3. The composition of claim 2, wherein said polyethylene glycol is a branched polyethylene glycol.

4. The composition of claim 1, further comprising a pharmaceutically acceptable carrier.

5. The composition of claim 1, wherein the anti-tumor agent or antiviral agent is an anti-tumor agent.

6. The composition of claim 1, wherein the anti-tumor agent or antiviral agent is an anti-viral agent.

* * * * *